United States Patent
Barrera et al.

(10) Patent No.: US 9,416,163 B2
(45) Date of Patent: Aug. 16, 2016

(54) SYNTHETIC OLIGOPEPTIDES DESIGNED FROM MITE CYSTEINE PROTEASES AND METHODS FOR THE PRODUCTION OF POLYCLONAL IGY ANTIBODIES FOR THE DETECTION OF INTRADOMICILIARY MITES

(75) Inventors: Luis Alejandro Barrera, Puerto (CO); Eduardo Egea, Puerto (CO); Johana Espejo, Puerto (CO); Catalina Sosa, Puerto (CO); Elkin Navarro, Puerto (CO); Gloria Garavito, Barranquilla (CO); Dary Luz Mendoza, Barranquilla (CO); Leonardo Lareo, Puerto (CO); Luis Miguel Renjifo Martinez, legal representative, Bogotá (CO)

(73) Assignees: FUNDACION UNIVERSIDAD DEL NORTE, Barranquilla (CO); PONTIFICIA UNIVERSIDAD JAVERIANA, Bogota (CO)

( * ) Notice: Subject to any disclaimer, the term of this patent is extended or adjusted under 35 U.S.C. 154(b) by 0 days.

(21) Appl. No.: 13/256,918

(22) PCT Filed: Mar. 17, 2010

(86) PCT No.: PCT/IB2010/000554
§ 371 (c)(1),
(2), (4) Date: Dec. 28, 2011

(87) PCT Pub. No.: WO2010/146420
PCT Pub. Date: Dec. 23, 2010

(65) Prior Publication Data
US 2012/0107335 A1    May 3, 2012

(30) Foreign Application Priority Data
Mar. 17, 2009  (CO) ........................................ 027540
Mar. 2, 2010   (CO) ........................................ 024590

(51) Int. Cl.
| | | |
|---|---|---|
| A61K 38/00 | (2006.01) | |
| A61K 38/04 | (2006.01) | |
| A61K 39/00 | (2006.01) | |
| A61K 39/35 | (2006.01) | |
| A61K 39/36 | (2006.01) | |
| A61K 39/395 | (2006.01) | |
| C07K 5/00 | (2006.01) | |
| C07K 7/00 | (2006.01) | |
| C07K 16/00 | (2006.01) | |
| C07K 17/00 | (2006.01) | |
| C07K 14/435 | (2006.01) | |

(52) U.S. Cl.
CPC ........... *C07K 14/43531* (2013.01); *A61K 39/35* (2013.01); *A61K 38/00* (2013.01); *A61K 2039/55516* (2013.01)

(58) Field of Classification Search
None
See application file for complete search history.

(56) References Cited

U.S. PATENT DOCUMENTS

| | | | | |
|---|---|---|---|---|
| 5,820,862 A | * | 10/1998 | Garman et al. ............ | 424/184.1 |
| 7,288,256 B1 | * | 10/2007 | Garman et al. ............ | 424/184.1 |

FOREIGN PATENT DOCUMENTS

WO    WO-2007140505 A2    12/2007

OTHER PUBLICATIONS

Garavito et al. 'Generation and purification of polyclonal chicken IgY antibodies induced by synthetic oligopeptides against allergens of the group 1 dust mites.' J. Allergy Clin. Immunol. 123(2):Supp 1:p. 223, Abstract 862, 2009.*
Mao, Su-Yau. "Biotinylation of antibodies." Methods Mol Biol 34: 49-52, 1994.*
Lerner et al. 'Tapping the immunological repertoire to produce antibodies of predetermined specificity.' Nature. 299:592-596, 1982.*
Lederman et al. °A single amino acid substitution in a common African allele of the CD4 molecule ablates binding of the monoclonal antibody, OKT4. Molecular Immunology. 28:1171-1181, 1991.*
Garavito et al. 'Generation and purification of polyclonal chicken IgY antibodies induced by synthetic oligopeptides against allergent of the Group 1 dust mites.' Poster presented at Annual Meeting of the American Academy of Allergy, Asthma and Immunolgy held Mar. 13-17, 2009.*
PCT/IB2010/000554—International Search Report mailed Mar. 2, 2011.
EP Application No. 10789072.5—European Office Action (Coomunication pursuant to Article 94(3) EPC) mailed Jul. 2, 2014.
EP Application No. 10789072.5—European Office Action (Communication pursuant to Article 94(3) EPC) mailed Dec. 17, 2014.
EP Application No. 10789072.5—European Office Action (Communication pursuant to Article 94(3) EPC) mailed Jun. 2, 2015.

* cited by examiner

*Primary Examiner* — Nora Rooney
(74) *Attorney, Agent, or Firm* — Drinker Biddle & Reath LLP

(57) ABSTRACT

The invention refers to the design, synthesis and evaluation of 6 synthetic oligopeptides, that have not been previously described, designed from the T and B epitopes of allergens of group I of intradomiciliary mites of the species *Dermatophagoides pteronyssinus, Dermatophagoides farinae* and *Blomia tropicalis*, which can be used in the immunomodulation of individuals having immunocompetent systems and in the production of IgY polyclonal antibodies. The invention relates to a first method for obtaining a composition of IgY polyclonal antibodies that can be used as a diagnostic reagent having low cost and high reactivity in respect of intradomiciliary mites, and a second method for the detection of mite allergens, using the IgY antibody composition developed in the first method. The invention further relates to the composition of the IgY polyclonal antibodies.

19 Claims, 17 Drawing Sheets

FIG. 12

Figure 1A:
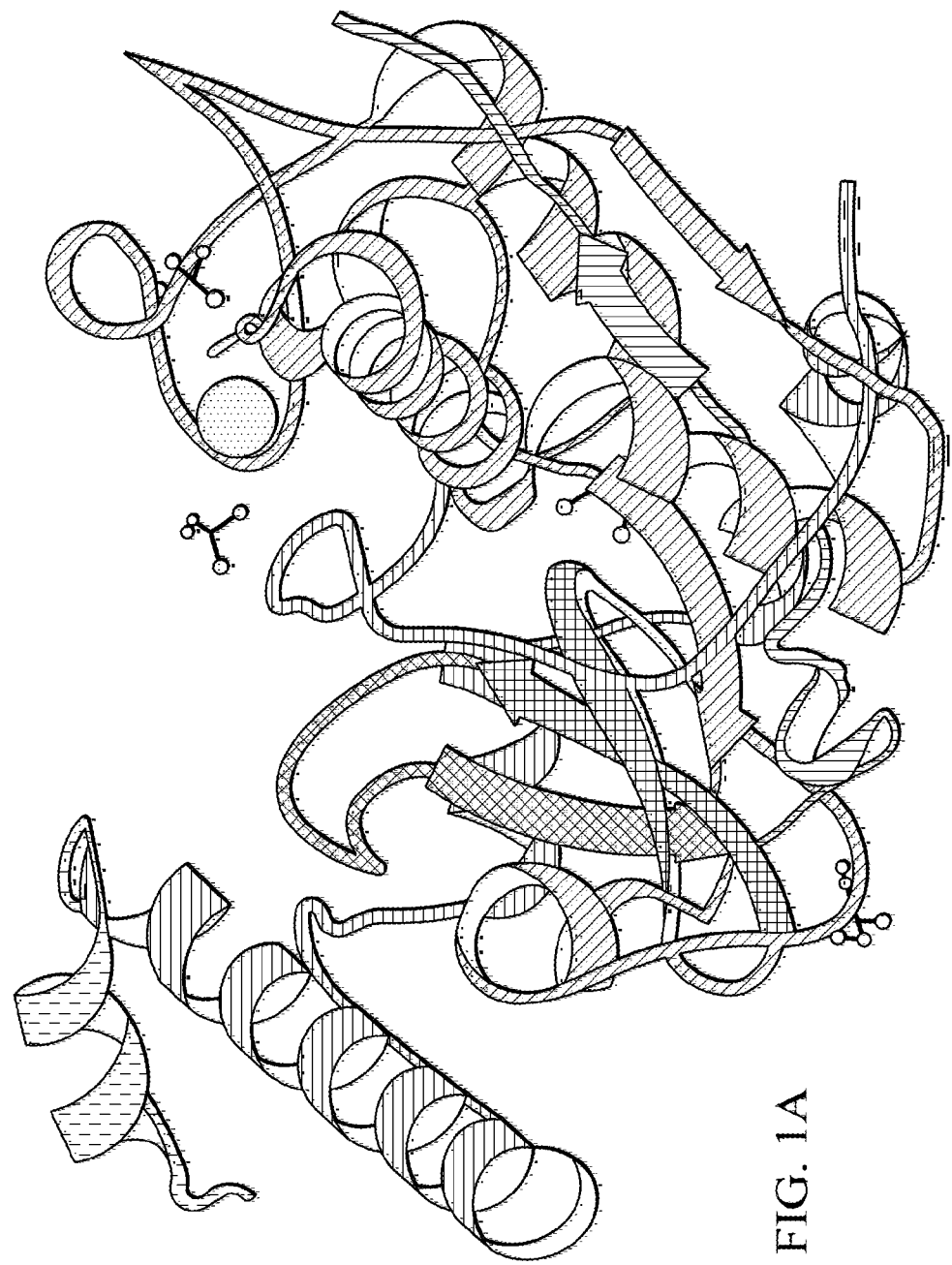

HOMOLOGY ANALYSIS OF SEQUENCES   MULTIPLE ALIGNMENT OF proDerp1, proDerf1, AND Blot 1 SEQUENCES

| SeqA | Name | Len(aa) | SeqB | Name | Len(aa) | Score |
|---|---|---|---|---|---|---|
| 1 | giproDerp1 | 320 | 2 | giproDerf1 | 321 | 83 |
| 1 | giproDerp1 | 320 | 3 | giBlot1 | 221 | 33 |
| 2 | giproDerf1 | 321 | 3 | giBlot1 | 221 | 34 |

CLUSTAL W (1.83) MULTIPLE SEQUENCE ALIGNMENT

```
SEQ ID NO:7 giproDerp1   MKIVLIAIASLLALSAVYARPSSIKTFEEYKKAFNKSYATFEDEEAARKNFLESVKYVQSN  60
SEQ ID NO:8 giproDerf1   MKFVLAIASLLVLSTVYARPASIKTFEEFKKAFNKNYATVEEEVARKNFLESLKYVEAN   60
SEQ ID NO:9 giBlot1

SEQ ID NO:7 giproDerp1   GGAINHLSDLSLDEFKNRFLMSAEAFEHLKTQFDLNAETNACSIN-GNAPAEIDLRQMRT  119
SEQ ID NO:8 giproDerf1   KGAINHLSDLSLDEFKNRYLMSAEAFEQLKTQFDLNAETSACRINSVNVPSELDLRSLRT  120
SEQ ID NO:9 giBlot1                                                   IPANFDWRQKTH    12
                                                                        * *.

SEQ ID NO:7 giproDerp1   VTPIRMQGGCGSCWAFSGVAATESAYLAYRNQSLDLAEQELVDCAS------QHGCHG  171
SEQ ID NO:8 giproDerf1   VTPIRMQGGCGSCWAFSGVAATESAYLAYRNTSLDLSEQELVDCAS------QHGCHG  172
SEQ ID NO:9 giBlot1      VNPIRNQGGCGSCWAFAAASSVAETLYAIHRHQNIILSEQELLDCTYHLYDPTYKCHGCQS   72
                         *.* ***********:*:   .*:  **  **:.:**:*** **        :* ***:.

SEQ ID NO:7 giproDerp1   DTIPRGIEYIQHNGVVQESYYRYVAREQSCRR-PNAQRFGISNYCQIYPPNVNKIREALA  230
SEQ ID NO:8 giproDerf1   DTIPRGIEYIQQNGVVEERSYPVAREQQCRR-PNSQHYGISNYCQIYPPDVKQIREALT  231
SEQ ID NO:9 giBlot1      GMSPEAFKYMKQKGLLEESHYPYKMLNQCQANARGTRYHVSSYNSLRYRAGDQEIQAAI  132
                                  :  :*  :* ** :  * .*         : *     :   ..*:

SEQ ID NO:7 giproDerp1   QTHSAIAVIIGIKDLDAFRHYDGRTIIQRDNGYQPNYHAVNIVGYSNAQGVDYWIVRNSW  290
SEQ ID NO:8 giproDerf1   QTHTAIAVIIGIKDLRAFQHYDGRTIIQHDNGYQPNYHAVNIVGYGSTQGVDYWIVRNSW  291
SEQ ID NO:9 giBlot1      MNHGPVVIYIHGTEA-HFRNLRKGILRGAGYNDAQIDHAVVLVGNGTQNGIDYWIVRTSW  191
                            .  *:  *    * : : **  :  .** *  :*** ::* :. :*:****.:*

SEQ ID NO:7 giproDerp1   DTNWGDNGYYFAANIDLMMIEEYPYVVIL  320
SEQ ID NO:8 giproDerf1   DTTWGDSGYYFQAGNNLMIEQYPYVVIM  321
SEQ ID NO:9 giBlot1      GTQWGDAGYGFVERHHNSLGINNYPIYASL  221
                          * ****.**  .   : : :*:**: ..
```

FIG. 13

MULTIPLE ALIGNMENT OF proDerp1, proDerf1, AND Blot 1 AND SEQ ID NO: 1 SEQUENCES

CLUSTAL W (1.83) MULTIPLE SEQUENCE ALIGNMENT

```
SEQ ID NO:7 giproDerp1    MKIVLAIASLLIALSAVYARPSSIKTFEEYKKAFNKSYATFEDEEAARKNFLESVKYVQSN   60
SEQ ID NO:1 giSeq4        ------------------------------------------------------------
SEQ ID NO:8 giproDerf1    MKFVLAIASLLVLSTVYARPASIKTEEEFKKAFNKNYATVEEEVARKNFLESLKYVEAN   60
SEQ ID NO:9 giBlot1       ------------------------------------------------------------

SEQ ID NO:7 giproDerp1    GGAINHLSDLSLDEFKNRFLMSAEAFEHLKTQFDLNAETNACSIN-GNAPAEIDLRQMRT  119
SEQ ID NO:1 giSeq4        ----------------------------------TNACSIN-GNAPAEIDLRQMR-     20
SEQ ID NO:8 giproDerf1    KGAINHLSDLSLDEFKNRYLMSAEAFEQLKTQFDLNAETSACRINSVNVPSELDLRSLRT  120
SEQ ID NO:9 giBlot1       --------------------------------------------IPANFDWRQKTH     12
                                                            *::::*  *.

SEQ ID NO:7 giproDerp1    VTPIRMQGGCGSCWAFSGVAATESAYLAYRNQSLDLAEQELVDCAS---------QHGCHG  171
SEQ ID NO:1 giSeq4        ------------------------------------------------------------
SEQ ID NO:8 giproDerf1    VTPIRMQGGCGSCWAFSGVAATESAYLAYRNTSLDLSEQELVDCAS---------QHGCHG  172
SEQ ID NO:9 giBlot1       VNPIRNQGGCGSCWAFAASSVAETLYAIHRHQNILSEQELLDCTYHLYDPTYKCHGCQS    72

SEQ ID NO:7 giproDerp1    DTIPRGIEYIQHNGVVQESYYRYVAREQSCRR-PNAQRFGISNYCQIYPPNVNKIREALA  230
SEQ ID NO:1 giSeq4        ------------------------------------------------------------
SEQ ID NO:8 giproDerf1    DTIPRGIEYIQONGVEEERSYPYVAREQQCRR-PNSQHYGISNYCQIYPPDVKQIREALT  231
SEQ ID NO:9 giBlot1       GMSPEAFKYMKQKGLLEESHYPVKMKLNQCQANARGTRYHVSSYNSLRYRAGDQEIQAAI  132

SEQ ID NO:7 giproDerp1    QTHSAIAVIIGIKDLDAFRHYDGRTIIQRDNGYQPNYHAVNIVGYSNAQGVDYWIVRNSW  290
SEQ ID NO:1 giSeq4        ------------------------------------------------------------
SEQ ID NO:8 giproDerf1    QTHTAIAVIIGIKDLRAFQHYDGRTIIQHDNGYQPNYHAVNIVGYGSTQGVDYWIVRNSW  291
SEQ ID NO:9 giBlot1       MNHGPVVIYHGTEAHFRNLRKG-ILRGAGYNDAQIDHAVVLVGWGTQNGIDYWIVRISW   191

SEQ ID NO:7 giproDerp1    DTNWGDNGYGYFAANIDLMMIEEYPYVVIL       320
SEQ ID NO:1 giSeq4        ------------------------------
SEQ ID NO:8 giproDerf1    DTTWGDSGYGYFQAGNNLMMIEQYPYVVIM       321
SEQ ID NO:9 giBlot1       GTQWGDAGYGFVERHHNSLGINNYPIYASL       221
```

FIG. 14

MULTIPLE ALIGNMENT OF proDerp1, proDerf1, AND Blot 1 AND SEQ ID NO: 2 SEQUENCES

```
CLUSTAL W (1.83) MULTIPLE SEQUENCE ALIGNMENT

SEQ ID NO:7 gi|proDerp1    MKIVLAIASLLALSAVYARPSSIKTFEEYKKAFNKSYATFEDEEAARKNFLESVKYVQSN   60
SEQ ID NO:8 gi|proDerf1    MKFVLAIASLLVLSTVVYARPASIKTFEEFKKAFNKNYATVEEEEVARKNFLESLKYVEAN   60
SEQ ID NO:2 gi|Seq1        ------------------------------------------------------------
SEQ ID NO:9 gi|Blot1       ------------------------------------------------------------

SEQ ID NO:7 gi|proDerp1    GGAINHLSDLSLDEFKNRFLMSAEAFEHLKTQFDLNAETNACSIN-QNAPAEIDLRQMRT  119
SEQ ID NO:8 gi|proDerf1    KGAINHLSDLSLDEFKNRYLMSAEAFEQLKTQFDLNAETSACRINSVNVPSELDLRSLRT  120
SEQ ID NO:2 gi|Seq1        ------------------------------------------------------------
SEQ ID NO:9 gi|Blot1       ------------------------------------IPANFDWRQKTH   12

SEQ ID NO:7 gi|proDerp1    VTPIRMQGGCGSCWAFSGVAATESAYLAYRNQSLDLAEQELVDCASQ------HGCHG  171
SEQ ID NO:8 gi|proDerf1    VTPIRMQGGCGSCWAFSGVAATESAYLAYRNTSLDLSEQELVDCASQ------HGCHG  172
SEQ ID NO:2 gi|Seq1        --PIRMQGGCGSCWAFSGV-----------------------------------------   17
SEQ ID NO:9 gi|Blot1       VNPIRNQGGCGSCWAFAASSVAETLYAIHRHQNITLSEQELIDCTYHLYDPTYKCHGCQS   72
                             *** **********

SEQ ID NO:7 gi|proDerp1    DTIPRGIEYIQHNGVVQESYYRVAREQSCRR-PNAQRFGISNYCQI-YPPNVNKIREAL  229
SEQ ID NO:8 gi|proDerf1    DTIPRGIEYIQQNGVVEERSYPVAREQQCRR-PNSQHYGISNYCQI-YPPDVKQIREAL  230
SEQ ID NO:2 gi|Seq1        ------------------------------------------------------------
SEQ ID NO:9 gi|Blot1       GMSPEAFKYMKQKGLLEESHYPYKMKLNQCQANARGTRYHVSSYNSLRYRAGDQEIQAAI  132

SEQ ID NO:7 gi|proDerp1    AQTHSAIAVIIGIKDLDAFRHYDGRTIIQRDNGYQPN--YHAVNIVGYSNAQGVDYWIVR  287
SEQ ID NO:8 gi|proDerf1    TQTHTAIAVIIGIKDLRAFQHYDGRTIIQHDNGYQPN--YHAVNIVGYGSTQGVDYWIVR  288
SEQ ID NO:2 gi|Seq1        ------------------------------------------------------------
SEQ ID NO:9 gi|Blot1       MN--HG--PVVIYHGTEAHFR-NLRKGILRGAGYNDAQIDHAVVLVGWTQNGIDYWIVR  188

SEQ ID NO:7 gi|proDerp1    NSWDTNWGDNGYGYFAANIDLMMIEEYPYVVIL  320
SEQ ID NO:8 gi|proDerf1    NSWDTTWGDSGYGYFQAGNNLMMIEQYPYVVIM  321
SEQ ID NO:2 gi|Seq1        ---------------------------------
SEQ ID NO:9 gi|Blot1       TSWGTQWGDAGYGFVERHHNSLGINNYPIYASL  221
```

FIG. 15

MULTIPLE ALIGNMENT OF proDerp1, proDerf1, AND Blot 1 AND SEQ ID NO: 3 SEQUENCES

```
SEQ ID NO:7 gi|511953|AAB60215.1|      ACSIN-GNAPAEIDLRQMRTVTPIRMQGGCGSCWAFSGVAATESAYLAYR 149
SEQ ID NO:8 gi|730035|P16311.2|PEPT1_DE ACRINSVNVPSELDLRSLRTVTPIRMQGGCGSCWAFSGVAATESAYLAYR 150
SEQ ID NO:3 gi|peptido1              ------------------------------------------------- 
SEQ ID NO:9 gi|14276828|AAK58415.1|    ---IPANFDWRQKTHVNPIRNQGGCGSCWAFAASSVAETLYAIHR  42

SEQ ID NO:7 gi|511953|AAB60215.1|      NQSLDLAEQELVDCASQ------HGCHGDTIPRGIEYIQHNGVVQESY 191
SEQ ID NO:8 gi|730035|P16311.2|PEPT1_DE NTSLDLSEQELVDCASQ------HGCHGDTIPRGIEYIQQNGVVEERS 192
SEQ ID NO:3 gi|peptido1              ------------------------------------------------- 
SEQ ID NO:9 gi|14276828|AAK58415.1|    HQNIILSEQELLDCTYHLYDPTYKCHGCQSGMSPEAFKYMKQKGLLEESH  92

SEQ ID NO:7 gi|511953|AAB60215.1|      YRYVAREQSCRR--PNAQRFGISNYCQI--YPPNVNKIREALAQTHSAIAVI 239
SEQ ID NO:8 gi|730035|P16311.2|PEPT1_DE YPYVAREQRCRR--PNSQHYGISNYCQI--YPPDVKQIREALTQTHTAIAVI 240
SEQ ID NO:3 gi|peptido1              ------------------------------------------------- 
SEQ ID NO:9 gi|14276828|AAK58415.1|    YPYKMKLNQCQANARGTRYHVSSYNSLRYRAGDQEIQAAIMN--HG--PVV 139

SEQ ID NO:7 gi|511953|AAB60215.1|      IGIKDLDAFRHYDGRTIIQRDNGYQPN---YHAVNIVGYSNAQGVDYWIVR 287
SEQ ID NO:8 gi|730035|P16311.2|PEPT1_DE IGIKDLRAFQHYDGRTIIQHDNGYQPN---YHAVNIVGYGSTQGDDYWIVR 288
SEQ ID NO:3 gi|peptido1              ------------------------------------DYWIVR    6
SEQ ID NO:9 gi|14276828|AAK58415.1|    IYIHGTEAHFR--NLRKGILRGAGYNDAQIDHAVVLVGWGTQNGIDYWIVR 188
                                                                           *******

SEQ ID NO:7 gi|511953|AAB60215.1|      NSWDTNWGDNGYGYFAANIDLMMIEEYPYVVIL 320
SEQ ID NO:8 gi|730035|P16311.2|PEPT1_DE NSWDTTWGDSGYGYFQAGNNLMMIEQYPYVVIM 321
SEQ ID NO:3 gi|peptido1              NSWDTNWGDNGYGY------------------  20
SEQ ID NO:9 gi|14276828|AAK58415.1|    TSWGTQWGDAGYGFVERHHNSLGINNYPIYASL 221
                                       .**.*.***.***:
```

Show Colors    View Alignment File

*PLEASE NOTE: Showing colors on large alignments is slow.*

FIG. 16

MULTIPLE ALIGNMENT OF proDerp1, proDerf1, AND Blot1 AND SEQ ID NO: 4 SEQUENCES

CLUSTAL 2.0.10 MULTIPLE SEQUENCE ALIGNMENT

```
SEQ ID NO:7  gi|511953|AAB60215.1|         MKIVLAIASLLALSAVYARPSSIKTEEEYKKAFNKSYATEEDEEAARKNF   50
SEQ ID NO:4  gi|Seq4                       ------------------------------------------------    
SEQ ID NO:8  gi|27530349|dbj|BAC53948.1|   MKFVLAIASLIVLSTVYARPASIKTEEFKKAFNKNYATVEEEEVARKNF   50
SEQ ID NO:9  gi|14276828|gb|AAK58415.1|    ------------------------------------------------

SEQ ID NO:7  gi|511953|AAB60215.1|         LESVKYVQSNGGAINHLSDLSLDEFKNRFLMSAEAFEHLKTQFDLNAETN  100
SEQ ID NO:4  gi|Seq4                       ------------------------------------------------    
SEQ ID NO:8  gi|27530349|dbj|BAC53948.1|   LESLKYVEANKGAINHLSDLSLDEFKNRYLMSAEAFEQLKTQFDLNAETS  100
SEQ ID NO:9  gi|14276828|gb|AAK58415.1|    ------------------------------------------------

SEQ ID NO:7  gi|511953|AAB60215.1|         ACSIN-GNAPAEIDLRQMRTVTPIRMQGGCGSCWAFSGVAATESAVLAYR  149
SEQ ID NO:4  gi|Seq4                       ------------------------------------------------    
SEQ ID NO:8  gi|27530349|dbj|BAC53948.1|   ACRINSVNVPSELDLRSLRTVTPIRMQGGCGSCWAFSGVAATESAVLAYR  150
SEQ ID NO:9  gi|14276828|gb|AAK58415.1|    ------IPANFDWRQKTHVNPIRNQGGCGSCWAFAASSVAELTYAIHR    42

SEQ ID NO:7  gi|511953|AAB60215.1|         NQSLDLAEQELVDCAS------QHGCHGDTIPRGIEYIQHNGVVQESY   191
SEQ ID NO:4  gi|Seq4                       ------------------------------------------------    
SEQ ID NO:8  gi|27530349|dbj|BAC53948.1|   NTSLDLSEQELVDCAS------QHGCHGDTIPRGIEYIQQNGVVEERS   192
SEQ ID NO:9  gi|14276828|gb|AAK58415.1|    HQNIILSEQELLDCTYHLYDPTYKCHGCQSGMSPEAFKYMKQKGLLEESH   92

SEQ ID NO:7  gi|511953|AAB60215.1|         YRYVAREQSCRR-PNAQRFGISNYCQIYPPNVKIREALAQTHSAIAVII  240
SEQ ID NO:4  gi|Seq4                       ------------------------------------------------    
SEQ ID NO:8  gi|27530349|dbj|BAC53948.1|   YPYVAREQQCRR-PNSQHYGISNYCQIYPPDVKQIREALTQTHTAIAVII  241
SEQ ID NO:9  gi|14276828|gb|AAK58415.1|    YPYKMKLNQCQANARGTRYHVSSYNSLRYRAGDQEIQAAIMNHGPVVIYI  142

SEQ ID NO:7  gi|511953|AAB60215.1|         GIKDLDAFRHYDGRTIIQRDNGYQPNYHAVNIVGYSNAQGVDYWIVRNSW  290
SEQ ID NO:4  gi|Seq4                       --------FRHYDGRTIIQRDNGYQPNY--------------------    20
SEQ ID NO:8  gi|27530349|dbj|BAC53948.1|   GIKDLRAFQHYDGRTIIQHDNGYQPNYHAVNIVGYGSTQGVDYWIVRNSW  291
SEQ ID NO:9  gi|14276828|gb|AAK58415.1|    HG-TEAHFRNLRKSILRGAGYNDAQIEHAVVLVGWGTQNGIDWIVRTSW   191
                                                   *  :

SEQ ID NO:7  gi|511953|AAB60215.1|         DTNWGDNGYFAANIDLMMIEEYPYVVIL   320
SEQ ID NO:4  gi|Seq4                       ---------------------------    
SEQ ID NO:8  gi|27530349|dbj|BAC53948.1|   DTTWGDSGYGFQAGNNLMMIEQYPYVVIM   321
SEQ ID NO:9  gi|14276828|gb|AAK58415.1|    GTQWGDAGYGFVERHHNSLGINNYPIYASL   221
```

FIG. 17

MULTIPLE ALIGNMENT OF proDerp1, proDerf1, AND Blot 1 AND SEQ ID NO: 5 SEQUENCES

CLUSTAL W (1.83) MULTIPLE SEQUENCE ALIGNMENT

```
SEQ ID NO:9 gi|Blot1     ------------------------------------------------------------
SEQ ID NO:5 gi|Seq11     ------------------------------------------------------------
SEQ ID NO:7 gi|proDerp1  MKIVLAIASLLALSAVYARPSSIKTEEEYKKAFNKSYATFEDEEAARKNFLESVKYVQSN  60
SEQ ID NO:8 gi|proDerf1  MKFVLAIASLLVLSTVYARPASIKTEEFKKAFNKNYATVEEEVARKNFLESLKYVEAN    60

SEQ ID NO:9 gi|Blot1     ------------------------------------------------IPANFDWRQKTH  12
SEQ ID NO:5 gi|Seq11     ------------------------------------------------IPANFDWRQKTH  12
SEQ ID NO:7 gi|proDerp1  GGAINHLSDLSLDEFKNRFLMSAEAFEHLKTQFDLNAETNACSIN-GNAPAEIDLRQMRT 119
SEQ ID NO:8 gi|proDerf1  KGAINHLSDLSLDEFKNRYLMSAEAFEQLKTQFDLNAETSACRINSVNVPSELDLRSLRT 120
                                                                         *  : :*  *.

SEQ ID NO:9 gi|Blot1     VNPIRNQGGGCGSCWAFAASSVAETLYAIHRHQNIILSEQELLDCTYHLYDPTYKCHGCQS  72
SEQ ID NO:5 gi|Seq11     VNPIRNQG----------------------------------------------------  20
SEQ ID NO:7 gi|proDerp1  VIPIRMQGGCGSCWAFSGVAATESAYLAYRNQSLDLAEQELVDCASQ-------HGCHG 171
SEQ ID NO:8 gi|proDerf1  VIPIRMQGGCGSCWAFSGVAATESAYLAYRNTSLDLSEQELVDCASQ-------HGCHG 172
                         *.****   **

SEQ ID NO:9 gi|Blot1     GMSPEAFKYMKQKGLLEESHYPYKMKLNQCQANARGTRYHVSSYNSLRYRAGDQEIQAAI 132
SEQ ID NO:5 gi|Seq11     ------------------------------------------------------------
SEQ ID NO:7 gi|proDerp1  DTIPRGIEYIQHNGVVQESYYRVARYEQSCRR-PNAQRFGISNYCQIYPPNVNKIREALA 230
SEQ ID NO:8 gi|proDerf1  DTIPRGIEYIQQNGVVEERSYPYVAREQQCRR-PNSQHYGISNYCQIYPPDVKQIREALT 231

SEQ ID NO:9 gi|Blot1     MNHGPVVIYHGTEAHFRNLRKG---ILRGAGYNDAQIDHAVVLVGWGTQNGIDYWIVRT 189
SEQ ID NO:5 gi|Seq11     ------------------------------------------------------------
SEQ ID NO:7 gi|proDerp1  QTHSAIAVIIGIKDLDAFRHYDGRTIIQRDNGYQPN--YHAVNIVGYSNAQGVDYWIVRN 288
SEQ ID NO:8 gi|proDerf1  QTHTAIAVIIGIKDLRAFQHYDGRTIIQHDNGYQPN--YHAVNIVGYGSTQGVDYWIVRN 289

SEQ ID NO:9 gi|Blot1     SWGTQWGDAGYGFVERHHNSLGINNYPIYASL 221
SEQ ID NO:5 gi|Seq11     --------------------------------
SEQ ID NO:7 gi|proDerp1  SWDTNWGDNGYGYFAANIDLMMIEEYPYVVIL 320
SEQ ID NO:8 gi|proDerf1  SWDTTWGDSGYGYFQAGNNLMMIEQYPYVVIM 321
```

FIG. 18

MULTIPLE ALIGNMENT OF proDerp1, proDerf1, AND Blot 1 AND SEQ ID NO: 6 SEQUENCES

CLUSTAL W (1.83) MULTIPLE SEQUENCE ALIGNMENT

```
SEQ ID NO:9 giBlot1      ------------------------------------------------------------
SEQ ID NO:6 giSeq9       ------------------------------------------------------------
SEQ ID NO:7 giproDerp1   MKIVLAIASLLALSAVYARPSSIKTFEEYKKAFNKSYATFEDEEAARKNFLESVKYVQSN    60
SEQ ID NO:8 giproDerf1   MKFVLAIASLLVLSTVYARPASIKTFEEFKKAFNKNYATVEEEVARKNFLESLKYVEAN    60

SEQ ID NO:9 giBlot1      -------------------------------------------IPANFDWRQKTH       12
SEQ ID NO:6 giSeq9       ------------------------------------------------------------
SEQ ID NO:7 giproDerp1   GGAINHLSDLSLDEFKNRFLMSAEAFEHLKTQFDLNAETNACSIN-GNAPAEIDLRQMRT  119
SEQ ID NO:8 giproDerf1   KGAINHLSDLSLDEFKNRYLMSAEAFEQLKTQFDLNAETSACRINSVNVPSELDLRSLRT  120

SEQ ID NO:9 giBlot1      ------------------------------------------------------------
SEQ ID NO:6 giSeq9       VNPIRNQGGCGSCWAFAAASSVAETLYAIHRHQNIILSEQELLDCTYHLYDPTYKCHGCQS   72
SEQ ID NO:7 giproDerp1   VIPIRMQGGCGSCWAFSGVGATESAYLAYRNQSLDLAEQEIVDCAS---------QHGCHG 171
SEQ ID NO:8 giproDerf1   VIPIRMQGGCGSCWAFSGVAATESAYLAYRNTSLDLSEQEIVDCAS---------QHGCHG 172

SEQ ID NO:9 giBlot1      ------------------------------------------------------------
SEQ ID NO:6 giSeq9       GMSPEAFKYMKQKGLLEESHYPYKMKLNQCQANARGTRYHVSSYNSLRYRAGDQEIQAAI  132
SEQ ID NO:7 giproDerp1   DTIPRGIEYIQHNGVVQESYYRYVAREQSCRRPNAQRFGISNYCQIYPPNVNKIREALAQ  231
SEQ ID NO:8 giproDerf1   DTIPRGIEYIQQNGVVEERSYPYVAREQQCRRPNSQHYGISNYCQIYPPDVKQIREALTQ  232

SEQ ID NO:9 giBlot1      MNHGPVVIYHGTEAHFRNLRKGILRGAGYNDAQIDHAVVLVGXGTQNGIDYWIVRTSWG  192
SEQ ID NO:6 giSeq9       -------------------AHFRNLRKGILRGAGYNDAQ-----------------------  20
SEQ ID NO:7 giproDerp1   THSAIAVIIGIKDLDAFRHYDGRTIIQRDNGYQPNYHAVNIVGYSNAQGVDYWIVRNSWD  291
SEQ ID NO:8 giproDerf1   THTAIAVIIGIKDLRAFQHYDGRTIIQHDNGYQPNYHAVNIVGYGSTQGVDYWIVRNSWD  292
                                            *  :                    :             :

SEQ ID NO:9 giBlot1      TQWGDAGYGFVERHHNSLGINNYPIYASL   221
SEQ ID NO:6 giSeq9       -----------------------------
SEQ ID NO:7 giproDerp1   TNWGDNGYGYFAANIDLMMIEEYPYVIL    320
SEQ ID NO:8 giproDerf1   TTWGDSGYGYFQAGNNLMMIEQYPYVVIM   321
```

SYNTHETIC OLIGOPEPTIDES DESIGNED FROM MITE CYSTEINE PROTEASES AND METHODS FOR THE PRODUCTION OF POLYCLONAL IGY ANTIBODIES FOR THE DETECTION OF INTRADOMICILIARY MITES

1. BRIEF DESCRIPTION OF THE INVENTION

This invention refers to the design, synthesis and evaluation of six synthetic peptides, not previously described, designed from sequences of natural proteins from allergens of domiciliary mites of group I of *Dermatophagoides pteronyssinus, Dermatophagoides farinae* and *Blomia tropicalis* species, which are capable to trigger specific immune responses. Therefore, this invention corresponds to six oligopeptide fragments, individually evaluated on their immunogenic effects, showing epitopes T and B of allergens Der p I, Der f I and Blo t I in their structure. Additionally, this invention refers to advantageous uses of these synthetic peptides and/or fragments thereof, in the development of diagnostic methods and immunomodulation protocols in patients with immunocompetent systems. The present invention is described in more detail in the following sections.

Also, the present invention corresponds to a first method for obtaining a composition of IgY antibodies useful as low cost diagnostic reagents having high reactivity against intradomiciliary mites, and a second method to detect mite allergens using the composition of IgY antibodies developed in the first method. The present invention also comprises the composition of IgY polyclonal antibodies as such.

The first method of the present invention allows obtaining a composition of IgY antibodies in a reproducible low cost fashion, capable of recognizing a wide range of intradomiciliary mite allergens from cysteine protease family.

The second method allows measuring total levels of allergens in indoor environments from samples contaminated and colonized by domiciliary mites. The level of allergens is determined by measuring changes in biophysical properties of reactants in identification systems, through immunochemical mechanisms, by comparison with reference standards.

2. STATE OF THE ART

Allergic diseases are characterized by high prevalence, morbidity and comorbidity. The use of synthetic peptides has become an active area of research and development that provides diagnostic tools and more effective treatments for such diseases. Evidence cited in literature shows that in Phase I and Phase II, peptides from hymenoptera, pollen and cat allergens, are effective in modulating the immune response in both experimental models and humans. The evidence here enclosed allow us to seek protection of six synthetic oligopeptides designed from the sequences of natural proteins of allergens from intradomiciliary mites of group I (1).

2.1. Allergens

Allergens are molecules, usually of proteic nature, which in atopic individuals, the immune system recognizes as "foreign," different than owns antigenic polymorphism, inducing an exaggerated Th2 adaptive immune response with the secretion of IL-4, IL-5 and IL-13, promoting the production of high amounts of allergen-specific IgE antibodies in B lymphocytes, which in subsequent contacts to the same immunogen will produce the release of chemical mediators, in particular histamine, which produce the typical symptoms of allergic reactions. Allergenic proteins in general exhibit two or three different molecular properties: the sensitizing property, i. e. inducing the immune system to produce an adaptive immune response of high-affinity IgE antibodies; and the ability to cause an allergic inflammatory response, that is, triggering signs and symptoms characteristic of allergic disease in previously sensitized individuals. Additionally, an allergen has the ability to link specific IgE antibodies. An allergen is a protein that commonly induces an exaggerated immune response mediated by IgE antibodies in genetically predisposed individuals. (1)

Analysis of protein databases suggest that the universe of allergens comprises more than 120 distinct families of proteins. (2) Many proteins can have a biological activity that influences the immune response. However, the majority of purified allergens have no effects on the skin, digestive tract, nose, among others, in non-allergic individuals. (3) Allergens are derived from proteins with a variety of biological functions, including enzymes, binding proteins, structural proteins, lipid transfer proteins, profilins, calcium-binding proteins, and others. The biological function of proteolytic enzymes of intradomicilliary dust mites, directly influence the development of IgE responses and can initiate inflammatory processes in the lung and other target organs, which are associated with asthma. Structural and biological characteristics may also influence the period that allergens persist in indoor and outdoor environments, as well as the conservation of allergenicity in the digestive tract. (4)

2. 1. 1. Molecular Characteristics of Allergenic Proteins

The molecular structure of allergenic proteins present immunodominant regions called epitopes, which interact with antigen-binding fragments (Fab) of specific IgE antibodies. Fab-allergen immune complexes have between 15 and 22 amino acid residues. Of these, only from 3 to 5 residues contribute to the binding process through multiple complementary noncovalent bonds, caused by electrostatic forces, mainly of van der Waals type. (5,7)

At present, there are many researches to determine whether intrinsic characteristics of epitopes are related to their allergenicity. That is, if molecular complexity (amino acid sequence, secondary structure, and folding type) as well as solubility, stability, size, and biochemical activity of an allergen, promote the necessary immunologic conditions for sensitization of the host's immune system, the interaction with IgE antibodies and the induction of allergic reactions (allergenicity). (8)

2. 1. 2. Allergens Stemming from Intradomiciliary Dust Mites

Mites are small arthropods belonging to the Arácnida, class; they have four pairs of legs, no body segmentation and lack antennas. They are distributed worldwide, adapted to living in different environments. Among the numerous species, there are those that live in house dust and base their nutrition on human and animal detritus (9).

*Dermatophagoides pteronyssinus* is the most important intradomiciliary mite species in Western Europe, Australia, England and New Zealand. *Dermatophagoides farinae* is the predominant mite in the United States and Japan, but *D. pteronyssinus* is more prevalent in some regions of these countries. (10-11), but infestation with either mite species depends not only on geographic location but also on environmental conditions of each household. Mite *Blomia tropicalis* is important in tropical and subtropical regions, particularly in South America and Southeast Asia. (12). Species of *Dermatophagoides* and *Blomia* genre are evolutionarily diverse and so have low cross-reactivity in proteins, because they have dissimilar amino acid sequences. (13)

Allergens from dust mite have been divided into groups according to the proteins' biologic function. Group I allergens (Der p 1, Der f 1 and Blo t 1) are cysteine proteases with a preference for substrates with a large hydrophobic side chain at position P2 or basic residues, that can act as mite's digestive enzymes and are found in high concentrations in the feces of the same (particles of 10-20 microns in diameter) (13). Der p1 allergen is a protein of 320 aa, with a molecular weight of 36104 Da (Cod NCBI AAB60215) (SEQ ID NO: 7). Der f 1 allergen is a protein of 321 aa, with a molecular weight of 36391 Da (NCBI Cod P16311) (SEQ ID NO: 8). Blo t 1 allergen is a protein of 221 aa, with a molecular weight of 25126 Da (Cod NCBI AAK58415) (SEQ ID NO: 9)

Allergens of the same group have a high degree of homology in their amino acid sequence, which is why the phenomenon of cross-reactivity presents, that happens when antibodies originally enhanced to allergens, bind or recognize an epitope (fraction) in a similar protein from a different resource. Thus, interaction with such homologous proteins can trigger allergic reactions or may be completely irrelevant to the patient (27).

Domestic house dust mites are complex organisms and they produce thousands of different proteins and other macromolecules. To date, more than 21 groups of allergens have been characterized in nine different species of mites and have been classified according to their biochemical identity. The first mite allergen described was Der p 1 from *Dermatophagoides pteronyssinus* (16). Der f 1 was then characterized by various researchers. Der p 1 was also the first allergen with which a cDNA analysis was developed. cDNA analysis revealed that they are cysteine proteases of the same papain and actinidin family. (28) From these studies with allergen extracts, allergens of group 1 have been identified as major allergens that bind IgE from subjects allergic to dust mites with high frequency. These proteins are present in high concentrations in feces of dust mites. The proteolytic activity of these cysteine proteases, has been proposed to increase their ability to sensitize human beings (29). IgE directed against Der p 1 is notably in the range of 50-70% in the serum of the same allergic patients (30).

2. 1. 3. Cysteine Proteases of Domiciliary Mites. Biologic and Molecular Characteristics Proteases are grouped into clans and families. Clans are groups of families with evidence of a common ancestry. Families are grouped by their catalytic type: A, aspartate; C, cysteine; G, glutamic acid, S, serine; T, threonine, and U, unknown. Serine, threonine and cysteine proteases use a nucleophile amino acid at their active site and form an acyl intermediate state and can also easily perform as transferases. (64)

The cysteine protease of the *D. pteronyssinus* mite (Der p 1) is a 25 kDa protein, encoded by a single gene, which has frequent polymorphisms, that have already been sequenced. (26) They have a prevalent variation in the alanine-valine sequence at position 124 and sporadic variations differing in 2 to 3 residues are apparent. (57-59)

The open reading frame encodes a 18 aa signal peptide, an 80 aa pro-peptide, and the region of the mature protein comprises 222 aa. The sequence includes four potential sites for N-glycosylation, three in the mature sequence and one in the pro-peptide. Der p 1 is produced as an inactive enzyme that is activated after the separation of the pro-peptide. Besides inhibiting the activity of the pro-enzyme, the pro-peptide may also act as a folding platform for the maturation of Der p 1, as suggested for other proteases. When Der p 1 is extracted from mite feces, it is present in mature form (nDer p 1). (60-61)

Cysteine proteases are divided into five clans, each containing a number of families grouped according to the architecture of their catalytic dyad or triad. Der p 1 belongs to clan CA, family C1, which also includes papain and its relatives. The crystal structures of papain and several closely related proteases of this family have been determined, and catalytic residues have been identified as Cys, His, and Asn. In addition, a conserved Gln residue is essential for catalytic activity and is believed to help forming the oxyanion hole, which stabilizes the transition state during catalysis. (62).

Figure 1B:
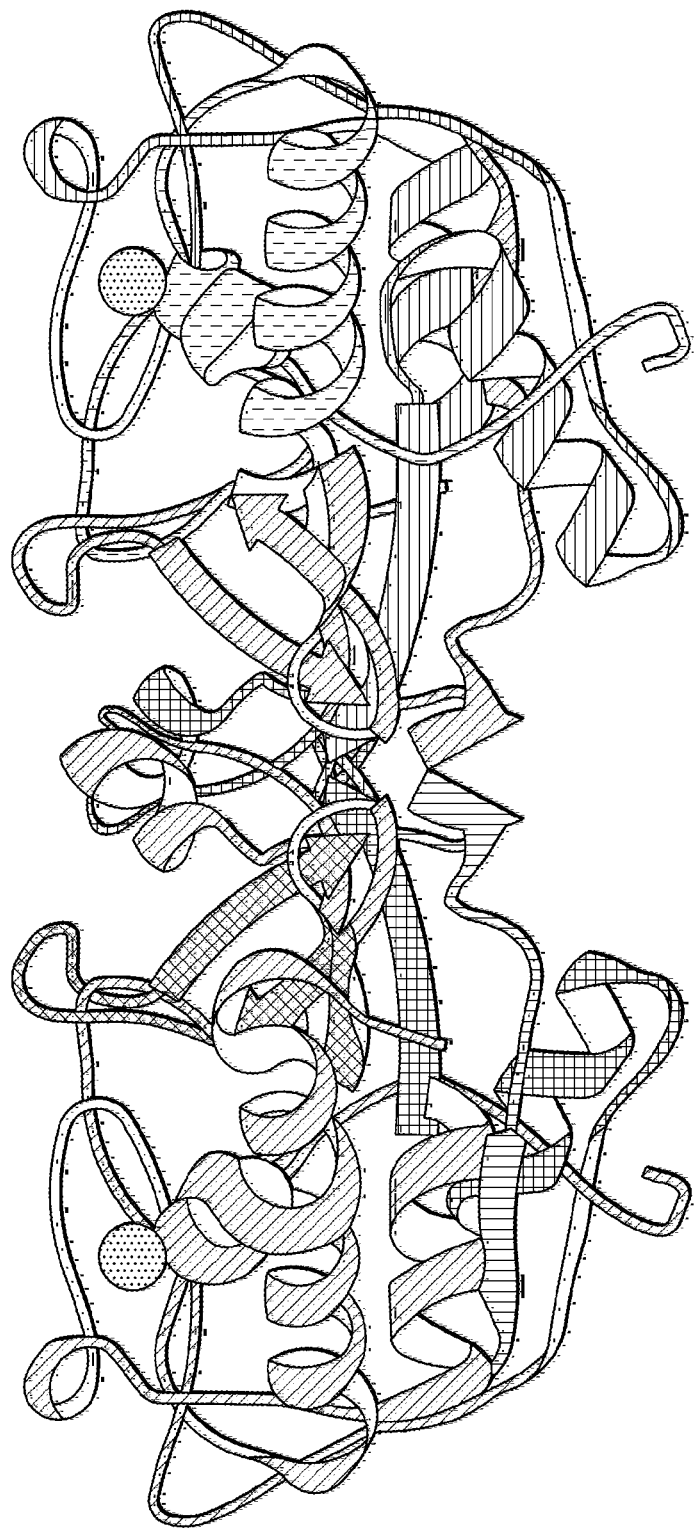

FIG. 1 shows the biological structure of Der p 1 A. proDer p 1 and B Der p 1 mature and fully active. (33) open sources: PDB.

Cys and His catalytic residues are believed to form a thiolate-imidazolium ion, stabilized by a direct hydrogen bond between the side chains of His and Asn catalytic residues. (64)

Most members of C1 family have pro-peptides homologous to papain's (115 aa), although length may vary. It is believed that the pro-peptide acts by hiding the active site and shielding access to substrates, thereby inhibiting enzyme activity. Proteolysis of the same is prevented by binding the pro-peptide in reverse direction compared to the substrate. When its sequence is aligned with the peptide of papain, the pro-peptide of Der p 1 has only 17 identical residues. (65)

The secondary structure of the cysteine protease of *Dermatophagoides pteronyssinus* mite is formed in 28% by alpha helices (8 helices, 63 residues) and in 23% by beta sheets (18 sheets, 53 residues) with different disulfide bonds that stabilize the protein. (See FIG. 2)

Molecular Epitopes of Der P 1 Protein.

The region between amino acids 15-33 of the mature protein is accessible to interaction with IgE antibodie paratopes, but it is relatively widespread and could constitute discontinuous epitopes with parts of the region between amino acids 188 to 199. Region 34-47, containing catalytic cysteine residues, is a helix buried within the molecule. The segment comprising residues 52 to 111 is well exposed on the surface and could be subdivided in small segments: 52-56, 60-80, 81-94, and 101-111, corresponding to linear epitopes or discontinuous epitopes. Epitope 81-94 consists of two continuous epitopes separated by amino acids 101 to 111, and the same is also exposed to the surface and constitutes an ideal linear epitope, as epitope 117-133. Region 155 to 175 is partially buried in a dimer interface and may be part of a discontinuous epitope with the adjacent segment 176 to 187, or with part of the segment 60 to 80. Finally, region 188 to 199 is compact enough to constitute a linear epitope or in combination with 15-33. There are variations in all described epitopes compared with Der f 1 and Eur m 1, with the exception of region 60-80, which is fully preserved with respect to Der f 1. (63)

At least 12 isoforms of Der p 1 have been reported (36). Amino acid residues within the propeptide mediate their association to the membrane, and play a role in the transport of the proenzyme to lysosomes. (67-68)

Intradomiciliary mites of group 1 consists of cysteine proteases of each of the different mites species. These proteins produce clear clinical symptoms in >80% of patients allergic to dust mites. Cysteine proteases from *Dermatophagoides pteronyssinus* (Der p 1), *Dermatophagoides farinae* (Der f 1), *Blomia tropicalis* (Blo t 1), microcrystalline *Dermatophagoides* (Der m 1) and *Euroglyphus maynei* (Eur m 1), have been characterized so far. (13). Among the proteins that produce clinical symptoms highlights Der p 1 cysteine protease, which is positive in 92% of patients allergic to dust mites by RAST (39) and Der f 1 which in 87% of patients allergic to mites elicits IgE antibody against Der f 1. (70)

Figure 2:
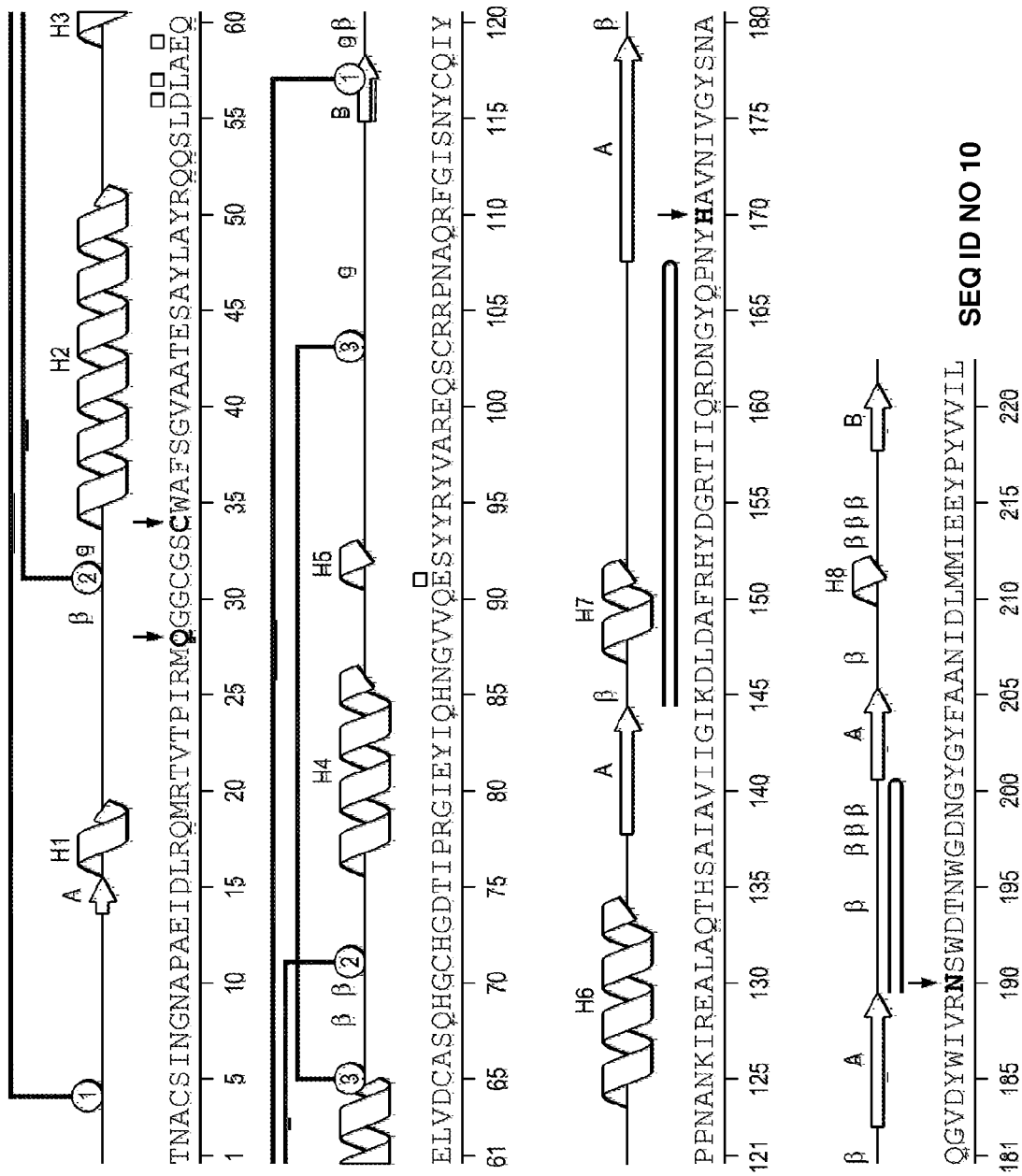

FIG. 2 Secondary structure of fully active Der p 1. (63) open sources: PDB.

These cysteine proteases have been implicated in human diseases such as cancer, rheumatoid arthritis, osteoporosis and Alzheimer's disease. (71) For this reason, we consider cysteine proteases from domiciliary mites as target molecules for the design of strategies for the diagnosis, treatment and control of allergic diseases. (72)

Cross-Reactivity Between Cysteine Proteases

Cross-reactivity phenomenon occurs when IgE antibodies, originally enhanced for an allergen, bind or recognize an epitope (fraction) in a similar protein from a different resource. Interaction with these homologous proteins can trigger allergic reactions or may be completely irrelevant to the patient. (73-75)

Intradomiciliary mites of Group 1 share structural features, which allow grouping them within CA clan, in C1 family, which also includes papain, mammal cathepsin (B, C, F, H, L, K, O, S, V, X and W) and their relatives. These proteins have highly conserved domains (see FIG. 3), which make that these allergenic proteins are recognized by IgE antibodies from patients sensitized against cysteine proteases from a different resource. That is, these proteins cross-react with each other, so a very diverse group of resources may elicit common allergic symptoms. (76-77) There is evidence that Der p I and Der f I have a cross-reactivity greater than 80%. (78-79).

Figure 3:
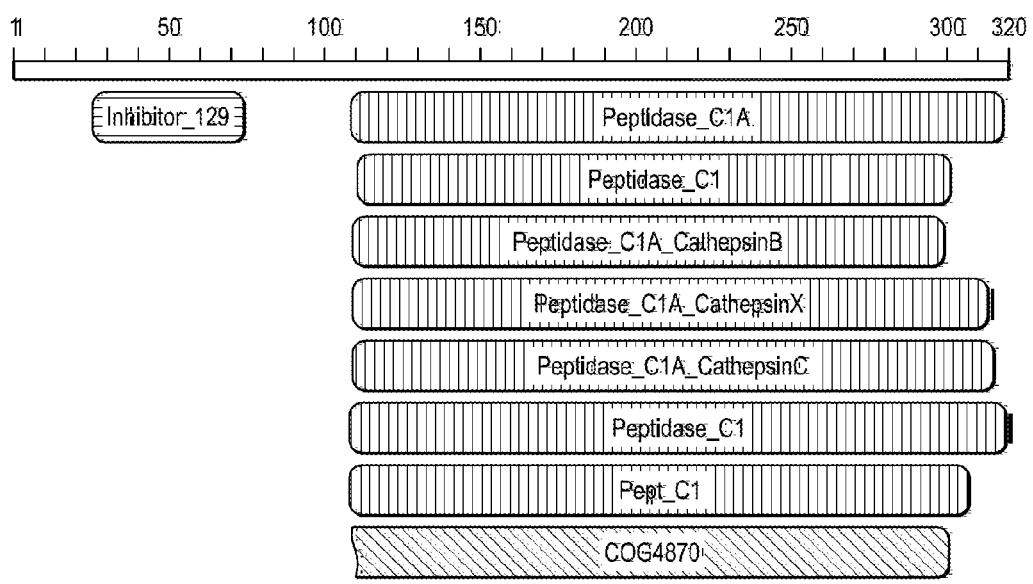

FIG. 3 shows conserved domains of pro Der p 1. (80) open sources: NCBI.

Other relevant resources having cross-reactivity with intra-domiciliary mites of group 1 include cathepsins, a group of lysosomal exopeptidases expressed in all human tissues, involved in protein degradation, antigen processing, proenzymes activation and apoptotic processes. (81-82). Plant cathepsins are used in the mobilization of reserve proteins. (83-85)

Immune Response to Cysteine Protease

Although there is a growing understanding of the mechanisms involved in the development of allergic inflammation, once sensitization has occurred, the mechanisms of interaction between Der p 1 and cell populations of the respiratory tract and its role in the sensitization process, are still unclear. (86)

Bronchial epithelium is the first barrier encountered by inhaled antigens, it provides an important link between the external environment and the interior of the body. Dendritic cell activation by inhaled antigens normally leads to the induction of inhalation tolerance rather than allergic inflammation. The mechanisms involved in the breakdown of this tolerance in allergic individuals is unknown. It has been shown that a short exposure to high concentrations of Der p 1 or prolonged exposure to low concentrations, caused degradation of tight junctions in bronchial epithelial cells in asthma patients and also in cells from individuals without asthma. This increases the epithelium permeability, which could favor penetration into respiratory tract mucosa, not only of Der p 1, but also of other antigens devoid of proteolytic activity, thereby increasing the probability of finding antigen presenting cells and cause sensitization. Such a phenomenon would explain why sensitization to antigens from domestic dust mite is often associated with sensitization to multiple antigens (87).

Exposure of respiratory tract epithelial cells to Der p1 induces secretion of pro-inflammatory cytokines, particularly (GM-CSF) and IL-6. The secretion of these mediators from bronchial epithelial cells of asthmatic patients is associated with intracellular transport of the allergen and occurs after a brief exposure to low concentrations of Der p 1. (88) Accordingly, cysteine protease catalytic activity of the house dust mite Der p 1 allergen is associated with increased permeability in the bronchial epithelium, thus facilitating its processing.

Figure 4:
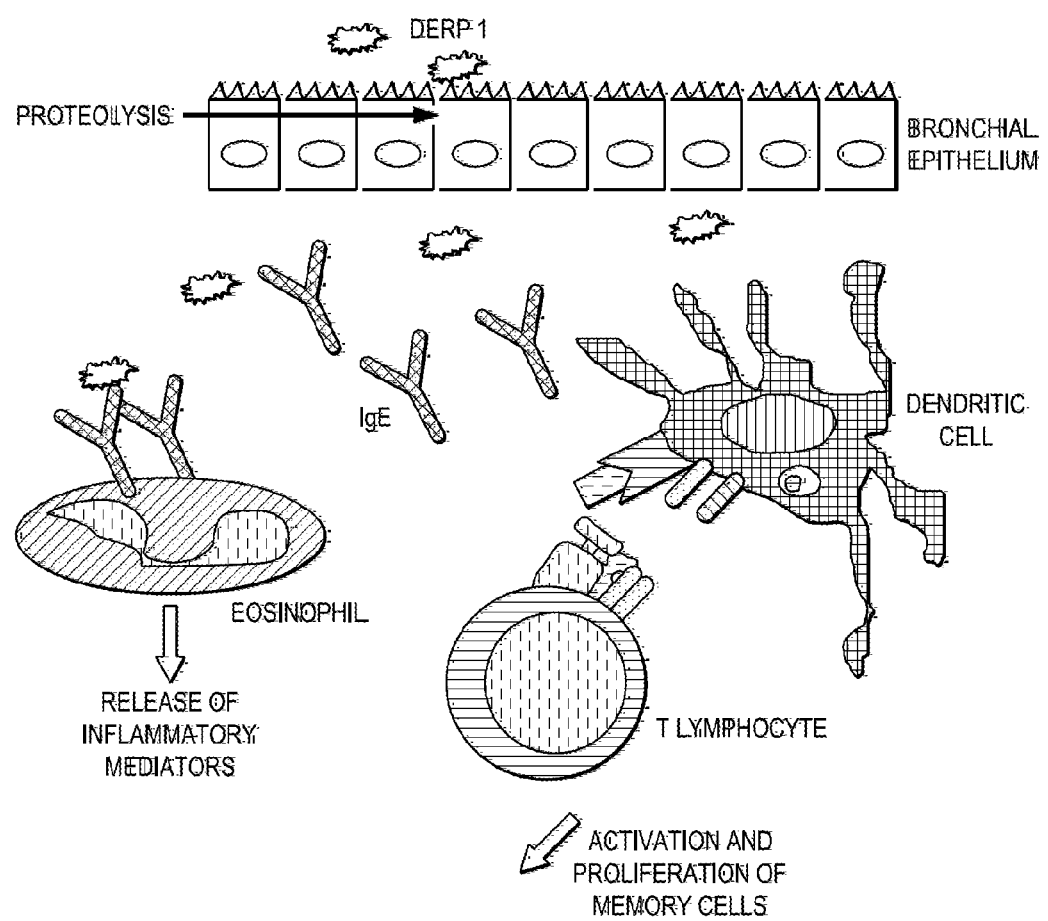

FIG. 4 shows the increment in membrane permeability by proteolytic action of Der p 1. (89)

This allergen is also capable of cutting CD23 (IgE's low affinity receptor, which regulates the synthesis of these immunoglobulins) and CD25 (interleukin-2 receptor α subunit). As a result of cleavage of surface CD25, proliferation of T lymphocytes from peripheral blood and IFN-γ secretion, decreases in response to stimulation. Th 1 and Th2 cell populations promote the development of the same cells subset while suppressing the propagation of the other subset. Therefore, CD25 induced cleavage by Der p 1, may lead to impaired growth of cells of Th1 subset and a consequent increase in Th2 subset. (113) This subset of T cells produce a cytokine profile including IL-4, IL-5, IL-6, and IL-13, that exert their effects on T cells, but also on other cell types including B lymphocytes and antigen presenting cells, such as monocytes and dendritic cells. IL-4 is useful as B lymphocytes growth factor and induces the production of IgE and $IgG_4$ isotypes. During the initial exposure to the allergen, T lymphocytes are stimulated, and production of IgE is induced; these antibodies bind to receptors on the surface of mast cells. (89-90).

2. 2. Intradomiciliary Mites and their Association with Allergic Diseases.

Epidemiological, clinical and immunological studies in Colombia, support the opinion that sensitization (specific IgE production against mite allergens and allergen-specific T-cell clones) for mite allergens is a cause of asthma and rhinitis, and not a simply triggering factor. These findings are consistent with those reported in literature. Previous studies in our country show that prevalence of mite antigen sensitization in asthmatic patients, in the city of Barranquilla, has a similar pattern to global behavior (80-85%). In the same studies, it is described that mite species most frequently found in patient's household ecosystems are: *Dermatophagoides farinae*, *Dermatophagoides pteronyssinus* and *Blomia tropicalis*. (2-4)

These arthropods are complex organisms in their protein composition. To date, more than 21 groups of allergens have been characterized in nine different species of mites, which have been classified according to their biochemical identity (5-6).

Intradomiciliary mites of Group 1, of interest in this research, is characterized by the presence of a cysteine proteases that causes clear clinical symptoms in more than 80% of patients allergic to dust mites. To date, biochemical and molecular characteristics of cysteine proteases from *Dermatophagoides pteronyssinus* (Der p 1), *Dermatophagoides farinae* (Der f 1), *Blomia tropicalis* (Blo t 1), of interest in this application, are known (7-8).

2. 3. Experimental Studies with Oligopeptides that Produce Immunomodulation.

There is evidence showing that synthetic peptides induce antigen-specific tolerance, as well as hypo-response in several murine models, both in autoimmune diseases and allergic diseases (9). Briner, et al., sensitized mice to cat allergen Fel d 1 and demonstrated the ability of allergen-derived peptides to inhibit the production of cytokines from Th2 cells (10). Hoyne et al., administered intranasal Der p 2 peptides to mice. Results showed a shift in Th2 response to Th1, after stimulation with the intact natural protein. (11) Astori, et al. administered oligopeptides with T cell epitopes form Bet v allergen {11} to CBA/J mice, and found proliferation of T cells specific to this allergen, which was inhibited by therapeutic treatments with the previously described epitope (12).

In another murine experimental model, Hymenoptera venom allergen, phospholipase A2 (PLA2; Api m 1), negatively modulated the specific synthesis of IgE, demonstrating the inhibition of its synthesis. Post-experimental IT confirms the modulation. (19) Taken together, the studies above support the use of oligopeptides from native allergen to modulate Th1/Th2 response and polarization of T cells.

2. 3. 1 Experimental Studies with Oligopeptides in Humans

There is considerable experimental evidence showing that peptide Immune Therapy (IT) with peptides modulates immune response. To date, we have developed studies with synthetic oligopeptides from 4 allergens: cat allergen Fel d 1, bee venom allergen Api m 1, ragweed pollen allergen Amb a 1 and allergen of Japanese cedar pollen Cry j 2. (13)

Early studies used a combination of two peptides from Fel d 1. (Allervax Cat, ImmuLogic Corp., Waltham, Mass.). Upon completion of IT treatment in these patients, significant improvement of symptoms in study subjects was shown (14).

In another placebo-controlled double-blind study with parallel groups, using Fel d 1 peptides or placebo, subcutaneous injections (4×250 ug) were weekly administered to 42 patients with rhinitis and/or allergic asthma to cat allergens, providing similar results to the previous study (15).

Further clinical studies were recently developed using mixtures of peptides of short of Fel d 1 sequence. These peptides were intradermally administered to patients with allergic asthma sensitized to Fel d 1. Improvement in symptoms with challenge tests were evidenced with this allergen in study subjects, but adverse effects were presented. Dose dependent asthma attacks were observed with a single injection of the mixture of 12 peptides, however tolerance to the challenge became evident after a few months. Additionally, in vitro evaluation of PBMC response to allergens, showed reduced production of cytokine of TH2 profile and marked secretion of IFN-g. (13-15)

The same mixture of 12 peptides was administered in increasing doses for two weeks in a double-blind placebo-controlled trial, to 24 asthmatic patients allergic to cat allergens. Afterwards, provocation testes were performed by inhaling PC20 methacholine and PD20 allergen. The treatment showed a significant reduction in both early-phase skin reactions and in late phase intradermal challenge with allergen. This same study also demonstrated a reduction in allergen-specific proliferative response, as well as a reduction in the production of cytokines of Th2 profile. Another important finding of this study was an increase in IL-10 production by PBMC. (13)

2. 4. IgY Polyclonal Antibody Production Using Synthetic Oligopeptides

Antibodies are proteins present in serum and tissues of vertebrates, which specifically bind to foreign molecules (antigens) in an adaptive immune response. They are a valuable tool in research with wide application as a diagnostic reagent and as a therapeutic tool for treating various diseases. Currently available antibodies are monoclonal or polyclonal antibodies, commonly produced in mammals such as rabbits, hamsters, goats, sheep and horses. The use of these animals have some difficulties: the first two mentioned species, which are the most used, generate small amounts of serum and the others are difficult to maintain because of their size, high diet costs and difficult handling (16). A current alternative is the production of polyclonal antibodies in chicken egg yolks (IgY). This technology has been widely used in immunology, biochemistry, biotechnology, human and animal health. Experimental allergology has shown that IgY antibodies are able to identify and quantify allergens from Brazil nuts, peanuts, native allergenic peptides from Fel d 1 and recombinant Amb a 1.

In the production and purification of polyclonal antibodies from mammals blood, low performance levels are obtained, with time-consuming procedures in many cases. Disadvantages of available techniques and concerns for animal rights, highlights the interest in developing alternative methods for producing antibodies. In the sense of animal protection, the use of birds for the production of antibodies represents an advance since no painful procedures for taking blood samples are necessary. This is replaced by the collection of eggs. Even though, the fact that immunized chickens transfer antibodies to egg yolk is known for a long time, this alternative antibodies production has attracted attention only in the last decade (17-20).

This large amount of antibodies produced in chicken egg yolk, very well stocked and very stable, facilitates their production and use in the detection of antigens for diagnosis in human medicine, as well as in the production of conjugates. In addition, it significantly reduces the number of animals used for production, compared to other species (21).

For example, Finlay W, et al., used avian immunoglobulin system to provide a rapid method for generating highly specific antibodies against recombinant Fel d 1 allergen and native Amb a 1 (22). Evaluation of the results by ELISA and Western blot showed that specific IgY antibodies against these allergens were obtained. Blais B W, et al., developed an enzymatic immunoassay, Dot blot for detecting peanut allergens, using IgY antibodies attached to polystyrene plates and revealed with anti-peanut allergen antibodies conjugated to peroxidase, and obtaining excellent results (23). WB Burton, in turn, used IgY in an ELISA sandwich to immunospecifically capture and detect allergenic proteins of Brazil nut, having good results and recommending it as a simple method that could support regulatory agencies in the food industry to avoid the presence of undeclared allergens in food and related products. The foregoing has shown that IgY antibodies are able to identify and quantify allergens in concentrations lower than 1 ppm in immunohistochemical assays. (24)

2. 5. IgY Technology in the Detection of Allergens

Airborne allergens are airborne particles capable of producing respiratory, skin or conjunctiva allergy. Substances that most often produce allergic problems by inhalation are: pollens, mold spores, different types of mites, cockroaches, animal epithelium and other substances that directly affect the respiratory mucosa through a series of immune processes. Most of airborne allergens are usually proteins or protein-bound substances. Most of them are soluble glycoproteins, with no special physical and chemical characteristics, except for a molecular weight between 10. 000 and 40.000 Da. The size of aeroallergens is also important. Best known allergens range between 1 and 60 um (91-93)

Protective mechanisms of the nasal mucosa and respiratory tract (through cilia that carry particles to the oropharynx, which are then swallowed and quickly denatured in the stomach) removed most of the larger particles so that only those of 3 mm or less are able to reach pulmonary alveoli. This explains a greater exposure of nasal and conjunctival mucous membranes and upper respiratory tract. However, since most of the particles, given their size, do not enter into terminal bronchi and alveoli, alternative mechanisms of respiratory tracts response must be considered. A clinically important aeroallergen must meet two circumstances: (1) have specific antigenic groups capable of causing hypersensitivity responses in humans, and (2) be present in sufficient concentration in the air, so that the exposure level is appropriate to trigger an immune response. These criteria, apparently simple, are not always achieved at the same time in many of potential allergenic particles. There are many airborne substances, from plant and animal origin, and such as chemicals products, that can cause allergic symptoms in sensitized human subjects. The individual response depends on many factors, both inherent to the allergic subject, and the allergen itself: state of the immune system, allergen dose, frequency and penetration route, physical and chemical characteristics, etc. Among the most important aeroallergens, there are intra-domicilliary mite proteins and cockroach. IgY antibodies were used by researchers at the Food and Drug Administration in Rockville, Md., USA for the identification and characterization of new allergens in extracts of whole body of *Blattella germanica* and *Periplaneta americana* showing great sensitivity and specificity for these antibodies. (95)

Researchers at the center of Biologics Evaluation and Research in Bethesda, Md., USA, developed an avian immunoglobulin system to produce recombinant antibodies highly specific for a particular allergen (recombinant Fel d 1 or native Amb a 1) or multiple allergens (recombinant Fel d 1 and native Amb a 1) from a minimum of experimental animals. The generated IgY antibody fragments proved to be efficient in the identification and quantification of allergens, compared to standard immunoassays. (96)

Food allergy occurs in 1-8% of the population. (96-97) The presence of undeclared allergens in food poses a serious risk to allergic individuals which can lead from mild to severe exposure reactions. In North America and Europe, food allergens commonly involved in allergic reactions include eggs, shellfish, milk, fish, soy, wheat, peanuts, walnuts, dried fruit (such as hazelnuts, Brazil nuts, etc.). (98-99)

Peanuts, walnuts, and other products with allergenic components are often used as ingredients in food processing to improve taste and nutritional quality, and their presence in such foods should be clearly marked to allow their identification by allergic individuals. Given the risk of inadvertent contamination of food with allergenic products during the manufacturing process, the food industry and regulatory agencies require tools to monitor the presence of allergens. (100)

In this sense, the Canadian Food Inspection agency developed a Dot Blot to detect peanut proteins in foods, using anti-peanut IgY antibodies, and bound peanut proteins were detected by sequential reactions with anti-IgY antibody conjugated with peroxidase and developed with a chromogenic substrate. The assay gave discernible results at concentrations as small as 0.03 ug/ml. While the exact threshold dose for adverse reactions in people sensitive to peanuts is not known, one study showed that a minimum intake of 100 mg of peanut protein can cause symptoms of an allergic reaction. (101) Therefore, this assay using IgY antibodies proved suitable for the detection of peanut protein to levels associated with an allergic reaction. The specificity of IgY antibodies against peanut proteins was confirmed in these experiments, where beans, lentils, red beans, as well as similar extracts of nuts, hazelnuts, Brazil nuts extracts were evaluated. (102) However, since Dot Blot is a test that did not allow us to establish precise dose-response characteristics, researchers at the Analytical Chemistry Center at the Institute for Agrobiotechnology, Konrad Lorenz, Tulln, Austria, developed an indirect competitive enzyme immunoassay based on IgY technology for the detection of hazelnut proteins in food, achieving a detection limit of 10 ug/l and a quantification limit of 30 ug/l. They also reported cross-reactivity with various foods including soy beans, rice, eggs, wheat. Cross-reactivity decreased with the purification of IgY antibodies. (103-104)

The tests described so far were designed to detect specific allergens. At the Canadian Centre for food inspection mentioned above, an immunochemical test for simultaneous detection of multiple allergenic proteins was designed, using anti IgY antibodies against hazelnut, Brazil nut, and peanut, obtaining detection limits between 1.0 and 0.1 ug/g; demonstrating the feasibility of designing immunochemical test with IgY antibodies against multiple allergens. (104-105)

It has been shown that exposure to allergens is a risk factor for the development of allergic respiratory diseases, as well as for the onset of symptoms and signs of allergic respiratory disease. At present, the reduction of allergen levels is promoted through various methods and techniques, all of them of limited use in developing countries. The concept of "Life with low-allergen levels" is being used in Europe and Canada. There are studies that support the reduction of morbidity and comorbidity when such environmental intervention protocols are implemented. Environmental monitoring of such levels at homes and workplaces is beneficial for patents, achieving an adequate control of spaces where daily activities are performed.

Conventional methods for detecting mites generally use monoclonal antibodies, which require high production times and costs.

3. DETAILED DESCRIPTION OF THE INVENTION

The invention described herein corresponds to the use of six synthetic allergenic oligopeptides from natural allergens of intradomiciliary mites of group I, as effective immunogens for inducing T and B lymphocyte responses in immunocompetent individuals. Because these protein fragments behave as T and B epitopes of Der p I, Der f I and Blo t I allergens, it would allow the use of these short synthetic peptide sequences as a strategy for the induction of peripheral tolerance and modulation of Th2/Th1 balance that will lead to the design of future therapeutic protocols in the management of these pathologies. Additionally, given their ability to function as antigens with good efficacy to bind specific antibodies, they are further used in the development of diagnostic tests to detect allergens of intradomiciliary mites of group I.

The invention is based on the evaluation and confirmation that the synthetic peptides described herein are immunogens that induce the production of specific antibodies for epitopes present in allergens of intradomiciliary mites of group I *Dermatophagoides pteronyssinus, Dermatophagoides farinae* and *Blomia tropicalis*. These peptides correspond to protein fragments designed and obtained from allergenic proteins of intradomiciliary mites of group I, Der p I, Der f I and Blo t I. Advantages of using these synthetic peptides include, but are not limited to their ability to induce immune-cell responses.

For this purpose, peptides of the present invention are included in compositions suitable for different routes of administration, for example, for parenteral administration and/or intramuscularly in a sterile aqueous solution. For intravenous administration, suitable carriers include physiological saline solution, bacteriostatic water, phosphate buffered saline (PBS), etc. Sterile injectable solutions can be prepared by incorporating the active compounds (synthetic peptides) in the required amount in an appropriate solvent, and/or suitable vehicle with one or more combinations of the above mentioned ingredients.

Without limiting to a particular mechanism, the six synthetic peptides of the present invention induce an immune response that allows the identification of allergens of intradomiciliary mites of group I and differentiating between *Dermatophagoides* spp. And *Blomia tropicalis* species. Peptides described herein are chemically pure and induce specific responses. The six synthetic peptides are free of biologically active material, cell suspensions, tissue debris or chemical precursors from chemical synthesis.

To determine the amino acid sequence homology between the synthetic peptides and natural proteins, the sequences were aligned for an optimal comparison. When one amino acid of a first sequence corresponded to one amino acid located on the second sequence, it was considered that these sequences were identical at this position. The number of amino acids that share identical positions determine the degree of homology between the compared sequences.

This invention in an experimental model that induces the production of antibodies, specific for allergens of epitopes of intradomiciliary mites of group I (*Dermatophagoides pteronyssinus, Dermatophagoides farinae* and *Blomia tropicalis*).

Manipulations of the sequences are included within the scope of the invention, these modifications can be carried out during translation or synthesis, for example: glycosylations, acetylation, phosphorylation, amidation, proteolytic cleavage, etc. Conservative amino acid substitutions can be made in peptides, in one or more amino acid residues unessential for immune response.

The present invention corresponds to six synthetic oligopeptides, immunogenic, designed from amino acid sequences of natural protein allergens of intradomiciliary mites of group I: *Dermatophagoides pteronyssinus, Dermatophagoides farinae* and *Blomia tropicalis*, which are linear epitopes with multiple applications such as the induction of polyclonal antibodies production. Sequences corresponding to each of the oligopeptide fragments and their corresponding identification numbers, which include sequences of 17, 18, 19 and 20 amino acids, depending on each specific case, are listed below:

Also, the present invention corresponds to a first method for obtaining a composition of IgY antibodies useful as a low cost and high reactivity diagnostic reagent for domiciliary mites, and a second method to detect mite allergen using the IgY antibody composition developed in the first method. The present invention also comprises the composition of IgY polyclonal antibodies.

The first method of the present invention allows producing a composition of IgY antibodies at low cost and in a reproducible manner, capable of recognizing a wide range of domiciliary mite allergens belonging to the family of cysteine proteases.

The second method allows determining total levels of allergens in indoor environments, from contaminated samples colonized by domiciliary mites. The level of allergens is determined by measuring changes in biophysical properties of reactants in identification systems, through immunochemical mechanisms when compared with reference standards.

3. 1. Peptide Design 3. 1. 1. Sequence Analysis

In order to determine sequence homology (similarity and identity. (Exhibit 1) amino acid sequences alignments were developed using BLAST software (Altschul S F, Madden T L, Schaffer A A, Zhang J., Zhang Z., Miller W., and. Lipman D J (1997) Gapped BLAST and PSI-BLAST: a new generation of protein database search programs. *Nucleic Acids Research* 25 (17): 3389-3402.) ClustalW (Higgins D., Thompson J., Gibson T., Thompson J D, Higgins D G, Gibson T J (1994) CLUSTAL W: improving the sensitivity of progressive multiple sequence alignment-through sequence weighting, position-specific gap penalties and weight matrix choice. *Nucleic Acids Research* 22: 4673-4680.) and Protscale (Gasteiger E., Hoogland C., Gattiker A., Duvaud S., Wilkins M R, Appel R D, Bairoch A., *Protein Identification and Analysis Tools on the ExPASy Server*; (In) John M. Walker (ed): The Proteomics Protocols Handbook, Humana Press (2005). pp. 571-607).

Results from this analysis (FIGS. 18-23) allows to establish homology regions among the three different allergens from group 1 of interest hereof. With this information, two universal peptides identified as Sequences 2 and 3 were designed. Dissimilar regions identified in the previous analysis supported the design of the four remaining peptides.

Brief Description of FIGS. 18-22 of Sequence Alignment.

FIG. 18. Shows the alignment of allergens of intradomiciliary mites of group 1 (proDer p 1, ProDer f 1 and Blo t 1), where a high degree of homology was observed between proDer p 1 and proDer f 1, with an identity percentage of 83% between proDer p 1 and Blo t 1, of 33% between proDer p 1 and Blo t 1, and of 34% between proDer f 1 and Blo t 1.

FIG. 19. Shows the alignment of allergens of intradomiciliary mites of group 1 (proDer p 1, proDer f 1, Blo t 1 and Seq No. 3), where Seq No. 2 shares 12 of its 17 amino acids.

FIG. 20. Shows the alignment of allergens of intradomiciliary mites of group 1 (proDer p 1, proDer f 1, Blo t 1 and Seq No. 4) where Seq No. 3 only shares 2 of its 20 amino acids, which would differentiate *Dermatophagoides* species and *Blomia* species.

FIG. 21. Shows the alignment of allergens of intradomiciliary mites of group 1 (proDer p 1, proDer f 1, Blo t 1 and Seq No. 5) where Seq No. 4 only shares 3 of its 20 amino acids, which would differentiate *Dermatophagoides* species and *Blomia* species.

FIG. 22. Shows the alignment of allergens of intradomiciliary mites of group 1 (proDer p 1, proDer f 1, Blo t 1 and Seq No. 6) where Seq No. 5 only shares 2 of its 20 amino acids, which would differentiate between *Dermatophagoides* species and *Blomia* species.

FIG. 23. Shows the alignment of allergens of intradomiciliary mites of group 1 (proDer p 1, proDer f 1, Blo t 1 and Seq No. 8) where Seq No. 6 only shares 3 of its 20 amino acids, which would differentiate between *Dermatophagoides* species and *Blomia* species.

Sequences corresponding to each of the six peptides object of the present invention are presented and identified below:

SEQ ID No. 1 DER P 1 UN1: Oligopeptide fragment designed from the homology region between proteins Derp 1, Derf 1 and Blot 1 and having the specific sequence

```
TNACSINGNAPAEIDLRQMR (20 aa)
```

SEQ ID N° 2 DER P 1 PUJ1 homologue.—Oligopeptide fragment designed from the homology region between proteins Derp 1, Derf 1 and Blot 1 and having the specific sequence

```
PIRMQGGCGSCWAFSGV (17 aa)
```

SEQ ID N° 3 DER P 1 PUJ2 homologue: oligopeptide fragment designed from the homology region between proteins Derp 1, Derf 1 and Blot 1 and having the specific sequence

```
DYWIVRNSWDTNWGDNGYGY (20 aa)
```

SEQ ID No. 4 DER P 1 PUJ3: oligopeptide fragment designed from the homology region between proteins Derp 1, Derf 1 and Blot 1 and having the specific sequence

```
FRHYDGRTIIQRDNGYQPNY (20 aa)
```

SEQ ID No. 5 BLO T 1 UN2: oligopeptide fragment designed from the homology region between proteins Derp 1, Derf 1 and Blot 1 and having the specific sequence IPANFDWRQKTHVNPIRNQG (19 aa)

SEQ ID No. 6 BLO T 1 PUJ4:—oligopeptide fragment designed from the homology region between proteins Derp 1, Derf 1 and Blot 1 and having the specific sequence AHFRNLRKGILRGAGYNDAQ (20 aa)

3. 1. 2. Mapping of Epitopes

In order to establish whether our sequences were reported in Immuneepitope database (NIAID-NIH), Epitope sequence and 3D structural homology and Epitope mapping viewer software were used (Beaver J E. Bourne P E, Ponomarenko J V. 2007. *EpitopeViewer: a Java application for the visualization and analysis of immune epitopes in the Immune Epitope Database and Analysis Resource (IEDB). Immunome Res* 3:3.) to determine if among the sequences of epitopes reported in these databases, to date, the sequences of the oligopeptides here described are identical to those described for proteins in this database, and to demonstrate the structural characteristics of the sequences in the three-dimensional structure of Der p1 (PDB) protein.

Previous experiences have allowed us to differentiate homologous enzymes of the same family by using the described methodology. The majority of the experience reported in literature regarding the modulation of the immune response, particularly related to allergic immune cascade, has been achieved with recombinant proteins and/or peptides. We can assure that, to date, there are no previous reports of the use of synthetic peptides of intradomiciliary mite allergens for producing specific adaptive responses in immunocompetent organisms.

The pharmaceutical industry is currently developing the search for new drugs and/or medications for biological therapy, including the use of complete proteins or recombinant peptides. The use of synthetic peptides originated from different allergens, capable of generating an adaptive immune response, represents an experimental model towards the achievement of these objectives Results of the analysis showing that the peptides object of the present invention have not been identified as epitopes in such databases, and that similar peptides have also not been reported, are presented below.

Peptide 1

FIG. 5A shows peptide 1, designed with base on allergenic proteins of group I. It has not been reported in "ImmuneEpitope" database, since it is not highlighted on orange.

We can see in FIG. 5B how peptide 1 has buried amino acids (blue), exposed amino acids (red), and half-exposed and half-buried amino acids (with no color). This sequence is found on the surface of the mature protein. (See 3D image)

Peptide 2

Figure 6:
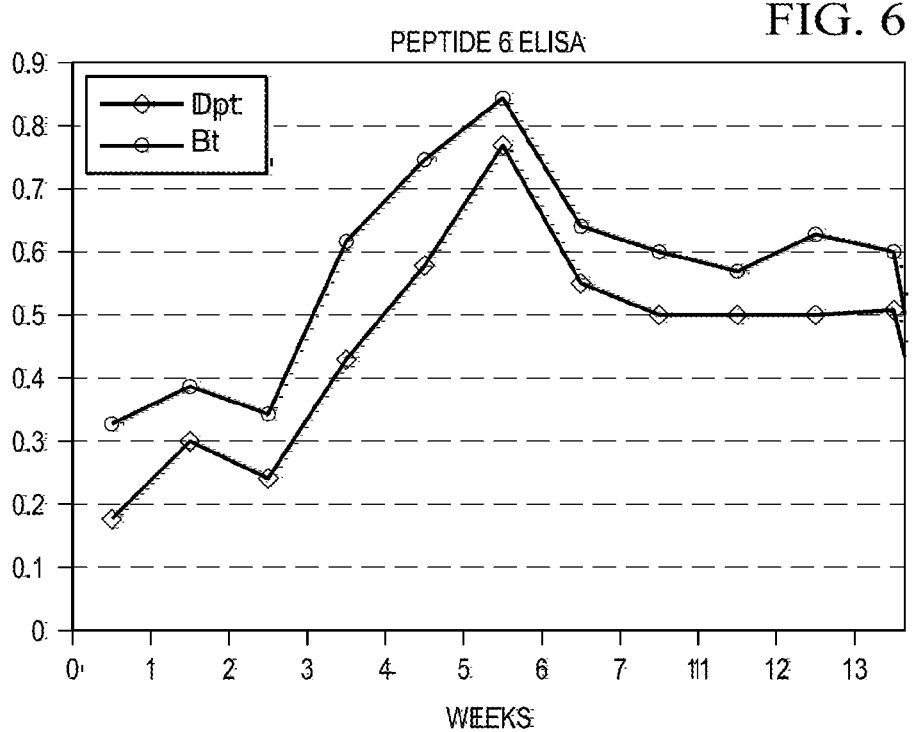

FIG. 6A shows peptide 2, designed with base on allergenic proteins of group I, found in the mature protein. It has not been reported in "ImmuneEpitope" database, since it is not highlighted in orange.

We can see in FIG. 6B how sequence 2, has buried amino acids (blue) exposed amino acids (red), and half-exposed and half buried amino acids (with no color). This sequence presents a large buried region, therefore it is possible that epitopes present in this sequence are located in amino acids between the proline (24) and the cisteine (31) of the mature protein. (See 3D image)

Peptide 3

Figure 7:
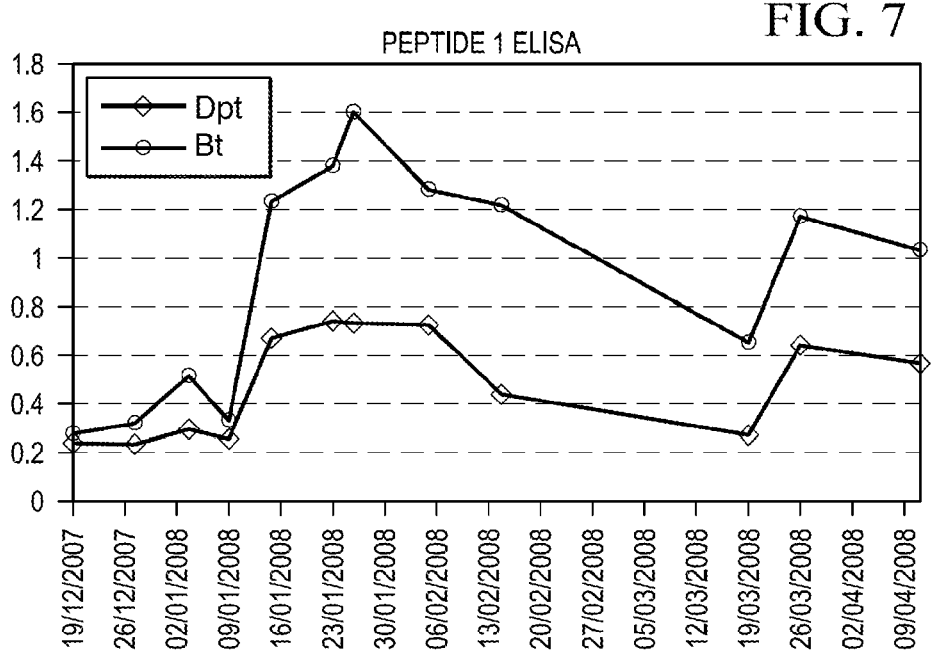

FIG. 7A shows Peptide 3, designed with base on allergenic proteins of group I. This sequence is found in the mature protein. This has not been reported in "ImmuneEpitope", database, since it does not appears in orange color.

FIG. 7B shows how the three dimensional structure of sequence 3 presents buried amino acids (blue) exposed amino acids (red) and partially exposed amino acids (without color). The sequence of peptide 1 is located on the surface of the mature protein. (See 3D image)

Peptide 4

Figure 8:
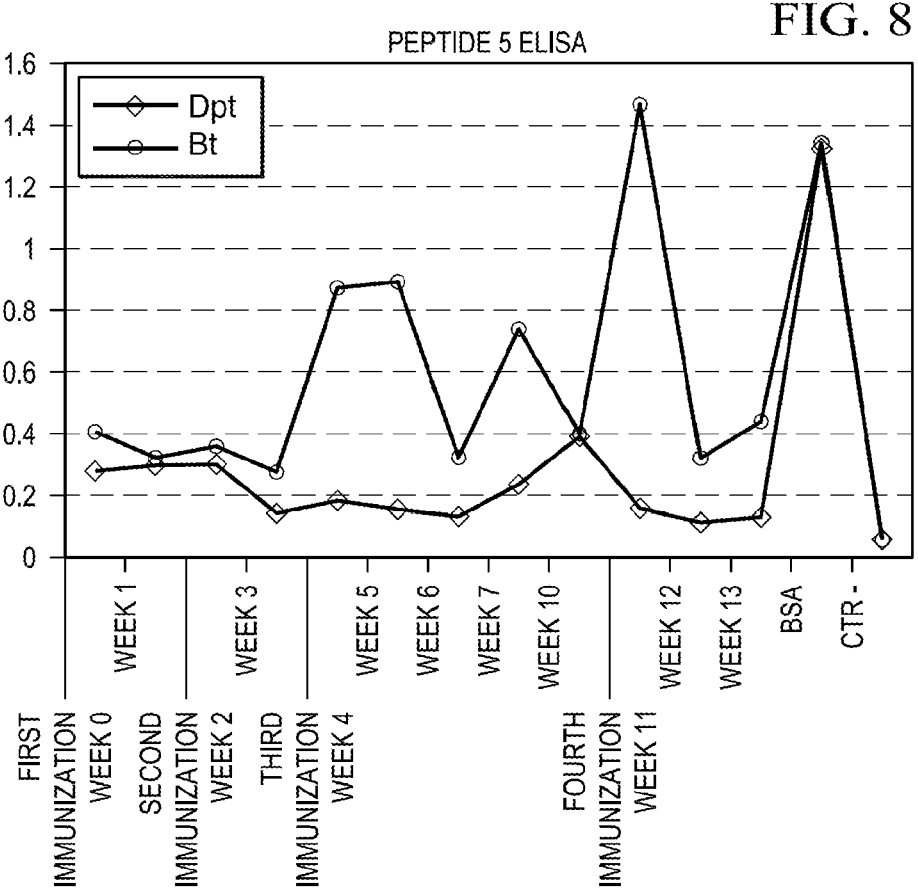

FIG. 8A shows peptide 4, designed with base on allergenic proteins of group I, this sequence is found in the mature protein. It has not been reported in immune epitope database, since it is not highlighted in orange.

We can see in FIG. 8B how sequence 4, has buried amino acids (blue) exposed amino acids (red), and half-exposed and half-buried amino acids (with no color). This sequence is found on the surface of the mature protein. (See 3D image)

Peptide 5

Figure 9:
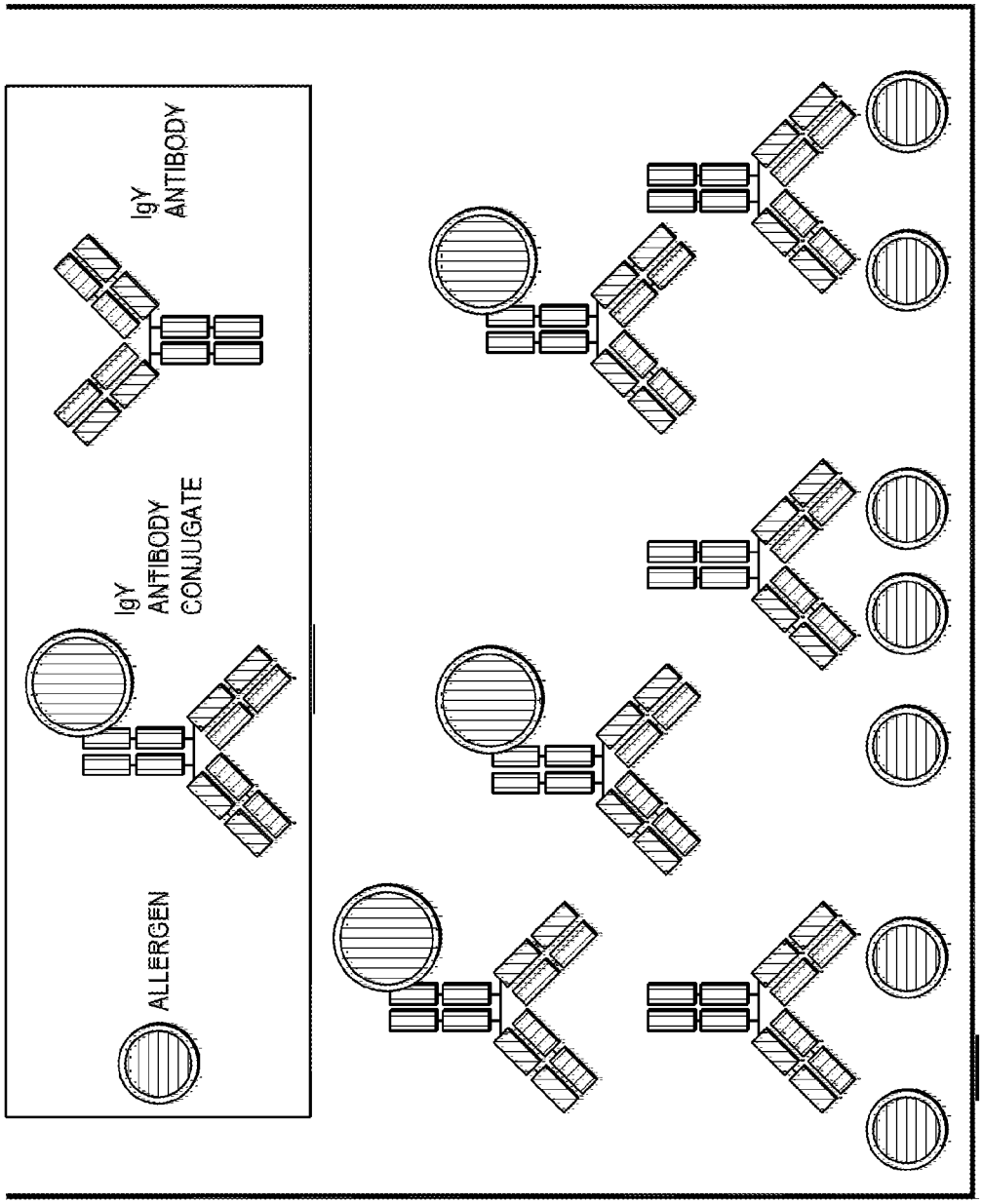

FIG. 9A shows peptide 5, designed with base on allergenic proteins of group I. It has not been reported in "ImmuneEpitope" database, since it is not highlighted in orange. The 3D structure of Blo t 1 has not been experimentally reported, for this reason, the mapping in the structure of the mature protein Der p 1 was performed, with which presented an identity of 37% (11 of 19 amino acids) (see second alignment). This graph shows how sequence 6 has buried amino acids (blue) exposed amino acids (red), and half exposed and half-buried amino (with no color), in FIG. 9B.

Peptide 6

Figure 10:
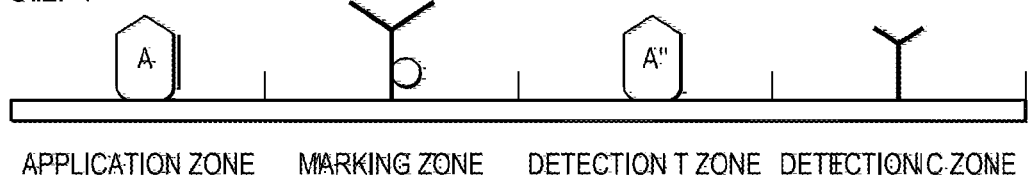
Figure 10:
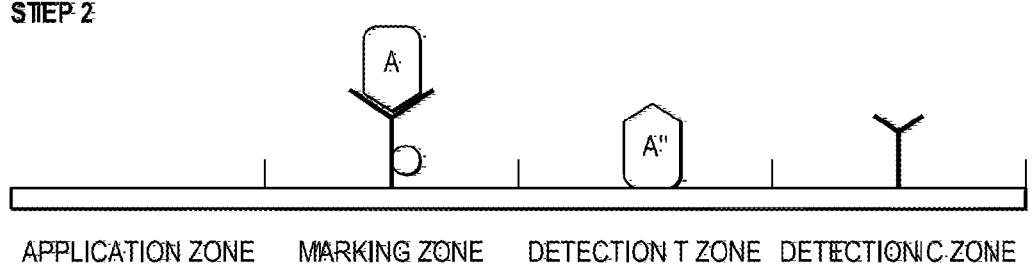
Figure 10:
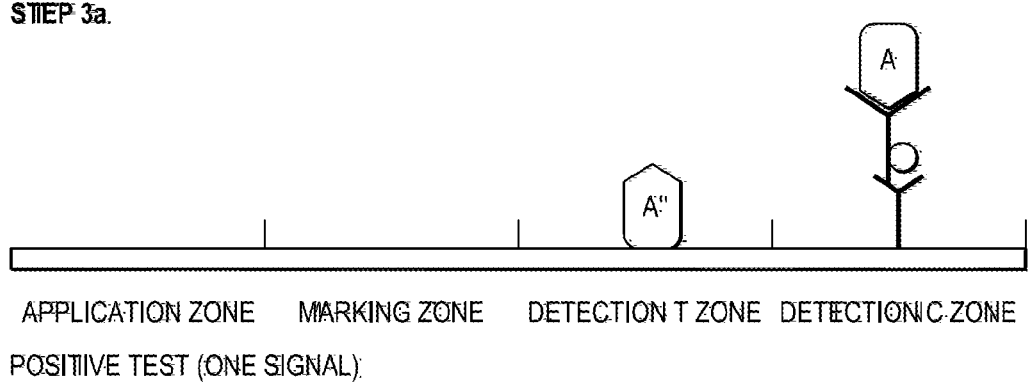
Figure 10:
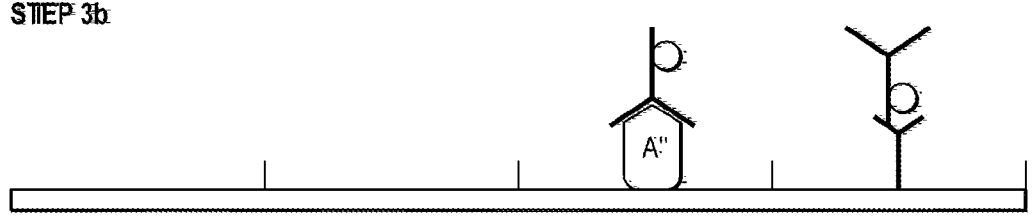
Figure 10:
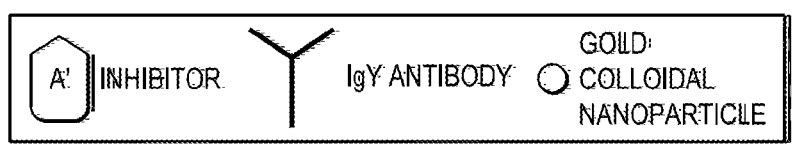

FIG. 10A shows Peptide 6, designed with base on allergenic proteins of group I. It has not been reported in "ImmuneEpitope database, since it is not highlighted in orange. The 3D structure of Blo t 1 has not been experimentally reported. This graph shows that sequence 5 has buried amino acids (blue) exposed amino acids (red), and half exposed and half buried amino acids (with no color), in FIG. 10B.

3. 1. 3. Description of the Synthesis of Peptides

The oligopeptides above described, were produced by chemical synthesis using F-moc chemistry on solid phase. The general principle of this method is based on repeated coupling and deprotection cycles using the 9H-(f)luoren-9-yl (m)eth(o)xy(c)arbonyl, as a protective group of the N-terminal end of growing peptides. Machine 396 from Advantace Chemtech was used, purified by FPLC chromatography and subsequently lyophilized. The purity of peptides was verified by: RP-HPLC using a Waters chromatograph. The identity of each of them was confirmed by mass spectrometry and their length ranged between 17 and 20 amino acids.

3. 1. 4. Immunogenicity Assessment:

EXAMPLE 1

Synthetic Oligopeptide—Peptide 2 (SEQ ID NO: 2)—Designed from Homologous Sequences of Allergens of Intradomiciliary Mites of Group I that Produce Polyclonal IgY Antibodies Anti Allergens of Intradomiciliary Mites of Group I Evaluated Peptide, Peptide 2 (SEQ ID NO: 2):

SEQUENCE: PIRMQGGCGSCWAFSGV

To demonstrate the immunogenicity capacity of this peptide, the use of this sequence in the production of specific antibodies is described. An experimental avian model was used in the experiments, represented by Hi Line Brown chickens, immunized with peptide 2, using complete Freund's adjuvant during the first immunization and incomplete Freund's adjuvant for the three subsequent immunizations, as described in the immunization protocol used. As a positive control, chickens were immunized with BSA, and as a negative control they were not immunized. Antibodies were extracted from egg yolk using an organic solvent and purified by thiophilic chromatography. Indirect ELISA tests were developed to measure the antibody titer and its specificity was determined by indirect ELISA. (25-26)

Results of a set of experiments that validate the immunogenicity of the peptide are presented below. As reactants, Dpt and Bt allergen extracts were used.

Figure 11:
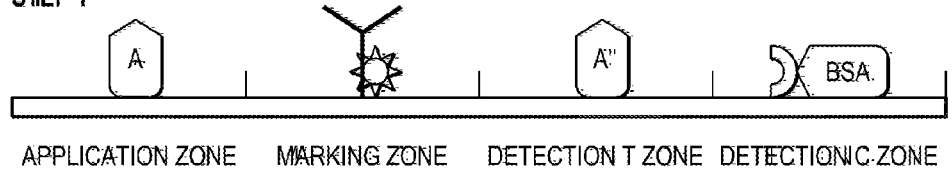
Figure 11:
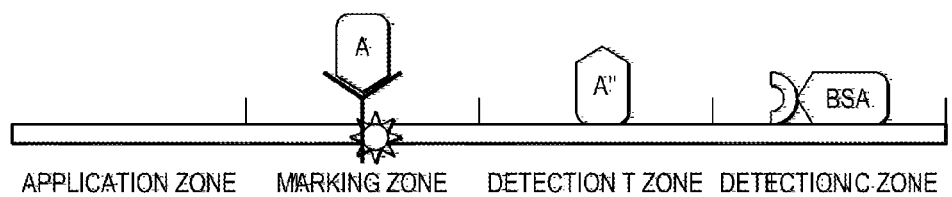
Figure 11:
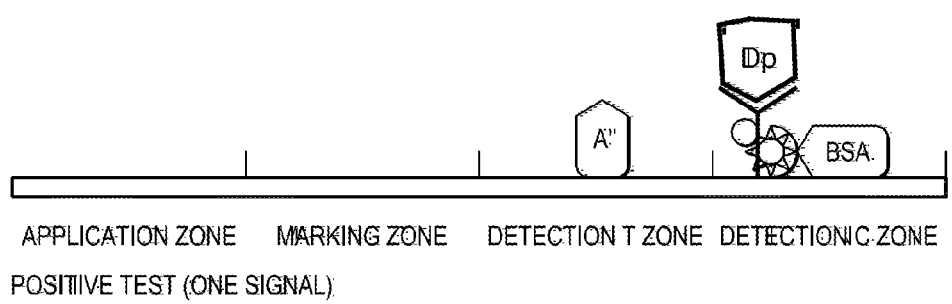
Figure 11:
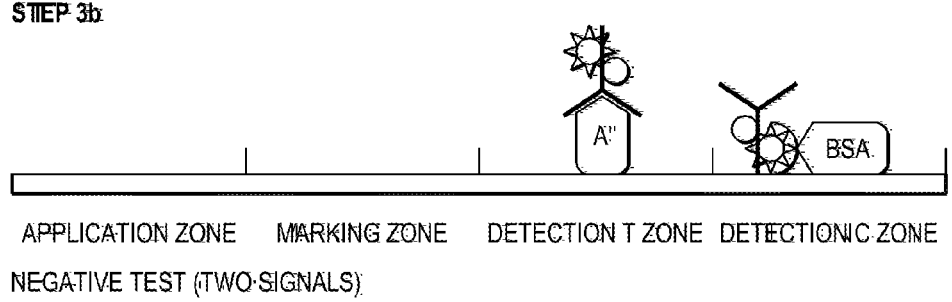
Figure 11:

FIG. 11 shows ELISA for peptide 2. Results show values of OPTICAL DENSITY (OD) resulting from the interaction of IgY anti-P02 antibodies with the used extracts.

Result:

During evaluation, OD for IgY anti P02 present a similar behavior to Dpt and Bt extracts. A higher OD is observed for these IgY anti P06 against Bt proteins. Higher DO peaks in the graph match for proteins of the three species studied.

Conclusions:

Synthetic oligopeptide P02 (universal peptide of intradomiciliary mite of group 1) induces the production of IgY anti P06 antibodies that recognize B and/or T epitopes in native proteins of intradomiciliary Df, Dp and Bt mite species.

EXAMPLE 2

Synthetic Oligopeptide—Peptide 6 (SEQ ID NO: 6)—Designed from the Sequence of Blo t 1 Allergen that Produce Polyclonal IgY Antibodies Anti Allergens of Intradomiciliary Mites of Group I Evaluated Peptide, Peptide 6 (SEQ ID NO: 6):

```
SEQUENCE: AHFRNLRKGILRGAGYNDAQ
```

To demonstrate the immunogenicity of this peptide, the use of this oligopeptide in the production of IgY antibodies that recognize Dp and Bt allergens is described. Experiments used an avian experimental model, represented by Hi Line Brown chickens, immunized with peptide 2, using complete Freund's adjuvant for the first immunization and incomplete Freund's adjuvant for the three subsequent immunizations described in the immunization protocol used. As a positive control, chickens were immunized with BSA, and as a negative control they were not immunized. Antibodies were extracted from egg yolk using an organic solvent and purified by thiophilic chromatography. Indirect ELISA tests were developed to measure the antibody titer and its specificity was determined by indirect ELISA. (25-26)

Indirect ELISAs were developed using Dpt and Bt extracts. IgY antibody anti P02 was assessed with the extracts. FIG. 12 illustrates the ELISA results for peptide 6.

Result: During evaluation, OD for IgY anti P02 present a similar behavior to Dpt and Bt extracts. A higher OD is observed for these IgY anti P02 against Bt proteins. Higher DO peaks in the graph match for proteins of the three species studied.

Polyclonal IgY antibodies specific for Dp and Bt intradomiciliary mites of group 1 species were produced using synthetic P02 oligopeptides.

Conclusions:

Synthetic oligopeptide P02 of intradomiciliary mites of group 1 induces the production of IgY anti P06 antibodies that recognize B and/or T epitopes in native proteins of Df and Bt mite species.

EXAMPLE 3

Synthetic Oligopeptide—Peptide 1 (SEQ ID NO: 1)—Designed from Sequences of Der p1 and Der f1 Allergens of *Dermatophagoides* Species that Produce Polyclonal IgY Antibodies Anti Allergens of Intradomiciliary Mites of Group I Evaluated Peptide, Peptide 1 (SEQ ID NO: 1):

```
SEQUENCE: TNACSINGNAPAEIDLRQMR
```

To demonstrate the immunogenicity of this peptide, the use of this oligopeptide in the production of IgY antibodies that recognize Dp and Bt allergens is described. Experiments used an avian experimental model, represented by Hi Line Brown chickens, immunized with peptide 4, using complete Freund's adjuvant for the first immunization and incomplete Freund's adjuvant for the three subsequent immunizations described in the immunization protocol used. As a positive control, chickens were immunized with BSA, and as a negative control they were not immunized. Antibodies were extracted from egg yolk with an organic solvent and purified by thophillic chromatography. Indirect ELISA tests were developed to measure the antibody titer and its specificity was determined by indirect ELISA. (25-26)(25-26)

Indirect ELISAs were developed using Dpt and Bt extracts. IgY antibody anti P04 was assessed with the extracts. FIG. 13 illustrates the ELISA results for peptide 1.

Experiment:

INDIRECT ELISAs were developed using Dpt and Bt extracts as antigens. Evaluated with crude extracts of IgY anti P04 antibodies.

Result:

During evaluation, OD for IgY anti P01 present a similar behavior to Dpt and Bt extracts. A higher OD is observed for these IgY anti P01 against Bt proteins. Higher DO peaks in the graph match for proteins of the studied species.

Specific polyclonal IgY antibodies of intradomiciliary mites of group 1 were produced using synthetic P04 oligopeptides.

Conclusions:

Synthetic oligopeptides P01 of intradomiciliary mites of group 1 induces the production of IgY anti P04 antibodies that recognize B and/or T epitopes in native proteins of intradomiciliary Df and Bt mite species.

EXAMPLE 4

Synthetic Oligopeptide—Peptide 5 (SEQ ID NO: 5)—Designed from the Sequence of Blo t 1 Allergen that Produce Polyclonal IgY Antibodies Anti Allergens of Intradomiciliary Mites of Group I Evaluated Peptide, Peptide 5 (SEQ ID NO: 5):

```
SEQUENCE: IPANFDWRQKTHVNPIRNQG
```

To demonstrate the immunogenicity of this peptide, the use of this sequence in the production specific antibodies is described. Experiments used an avian experimental model, represented by Hi Line Brown chickens, immunized with peptide 5, using complete Freund's adjuvant for the first immunization and incomplete Freund's adjuvant for the three subsequent immunizations described in the immunization protocol used. As a positive control, chickens were immunized with BSA, and as a negative control they were not immunized. Antibodies were extracted from egg yolk with an organic solvent and purified by thiophilic chromatography. Indirect ELISA tests were developed to measure the antibody titer and its specificity was determined by indirect ELISA (FIG. 14)

Experiment:

Indirect ELISAs were developed using Dpt and Bt extracts as antigens. Evaluated with crude extracts of IgY anti P05 antibodies.

Result:

DO for IgY anti P05 are significantly higher for Bt and Df compared with Dpt. It was possible to obtain specific polyclonal IgY antibodies from intradomiciliary mites of group 1 by using synthetic oligopeptides P05.

Conclusions:

Synthetic oligopeptide P05 of intradomiciliary mites of group 1 induces the production of IgY-anti P05 antibody that recognizes epitopes B and/or T in native proteins of intradomiciliary Dp and Bt mites.

3. 2. Method for Obtaining Polyclonal IgY Antibodies and the Detection Method of Mite Allergens.

One embodiment of the invention described herein corresponds to the method for obtaining a composition of IgY antibodies useful as a low cost and high specificity diagnostic reagent for the detection of domiciliary mite allergens. The invention also encompasses the composition of IgY antibodies.

The present invention also relates to a method for the detection of intradomiciliary mite allergens in dust samples from environments such as bedrooms, offices, kindergartens, hotels, cinemas, etc., using the composition of IgY polyclonal antibodies obtained using the first method described in this application, which is specific to allergens from mites of group 1 and allows the detection of allergens in low concentrations (up to 0.03 mg/mL).

With the first method of the invention it is possible to obtain polyclonal IgY antibodies with high specificity, that recognize intradomiciliary mite allergens, which are induced by special synthetic peptides, allowing directing them to particular regions of mite proteins. IgY polyclonal antibodies obtained in the present invention are the only IgY antibodies described to date, that are specific for intradomiciliary mite allergens, since anti-mite allergens antibodies previously described correspond to monoclonal antibodies. Synthetic peptides used in the method of the invention for obtaining IgY polyclonal antibodies are designed from different allergens from intradomiciliary mites of group 1 and, preferably, those of sequences SEQ ID No 1, SEQ ID No 2, SEQ ID No 3, SEQ ID No 4, SEQ ID NO 5, SEQ ID No 6, disclosed above.

Conventional methods for IgY antibody production uses natural and/or recombinant proteins, which produce antibodies against any region of the protein, affecting the reaction specificity. Synthetic peptides are chemically well defined compounds and, therefore, allow reducing interassay and intraassay variability. In contrast to antigens produced by culturing, synthetic ones allow performing studies with epitopes of difficult availability.

In this case, the use of synthetic peptides designed with base on natural proteins from intradomiciliary mites, preferably comprising or consisting in sequences SEQ ID No 1, SEQ ID No 2, SEQ ID No 3, SEQ ID No 4, SEQ ID NO 5, SEQ ID No 6, allows that these IgY antibodies bind characteristic molecular epitopes from different cysteine proteases of domiciliary mites, particularly cysteine proteases of *Dermatophagoides pteronyssinus*, *Dermatophagoides farinae*, and *Blomia tropicalis* mites, key players to trigger allergic respiratory disease in the tropics. Also, the use of IgY technology allows obtaining large volumes of IgY antibodies, which facilitates its massive use and transfer into the productive sector.

Additionally, the present invention provides a method for the detection of intradomiciliary mite allergens in dust samples, based on immuno enzymatic, immunochromatographic and/or electroblotting techniques, which uses the composition of antibodies developed in the present invention, which proved very efficient in detecting allergens of intradomiciliary mites of group 1 with a detection limit of 0.03 ug/ml.

The development of highly specific and good sensitivity polyclonal antibodies, allows the reliable detection of intradomiciliary mite allergens, at a lower cost than methods using monoclonal antibodies, but getting comparable results.

The method of detection of allergens in dust samples involves a sequence of operations going from the collection of dust samples, the production of the protein extract, and their assessment and analysis.

3. 2. 1. Method for Obtaining IgY Polyclonal Antibodies.

The first method of the invention, which leads to the manufacture of a composition of IgY polyclonal antibodies, useful as an inexpensive diagnostic reagent for domiciliary mites, involves the steps of:

a) preparing an immunogenic composition comprising at least one peptide with a homology greater than or equal to 85%, to a sequence selected from the group consisting of SEQ ID NO. 1, 2, 3, 4, 5 and 6;
b) hyperimmunizing chickens of Hy Line Brown variety, from 16 to 20 weeks of age;
c) extracting IgY polyclonal antibodies;
d) purifying IgY polyclonal antibodies.

In step a), for the preparation of the composition of peptides, between 50-150 ul of synthetic peptides are diluted in sterile water at a concentration between 100 and 300 ug/ml and homogenized with 50-150 ul of adjuvant.

In step b), for immunization of chickens, between 3 and 6 intramuscularly immunizations in the pectoral muscles (breast) are performed at intervals of 2-3 weeks for 2-3 months. The antigen (synthetic peptide) is injected at a concentration of 50-200 ug/ml, emulsified in complete Freund's® adjuvant for the first immunization (1-2), and in incomplete Freund's® adjuvant for subsequent reinforcements.

In step c), the isolation of antibodies is done by carefully separating the yolk from the white, and measuring volumes of both the yolk and the white. It is de-lipided using an organic solvent (e. g. chloroform). The content of the yolk is emulsified in 0.5 to 2 fold its volume in an aqueous buffer (e. g. PBS), subsequently, 1.5 to 3 volumes of organic solvent are added, and the mixture is incubated at room temperature between 1 to 3 hours, centrifuged at 2000-4000 rpm for 10-30 minutes at a temperature between 14 and 25° C., and the supernatant is collected and stored for further purification.

In step d) the purification is performed by column chromatography, e. g. thiophilic chromatography. In this case a CL4B Sepharose support activated with divinylsulfone (DVS) coupled to β-mercaptoethanol (β-MESH) is used, the active support is balanced in phosphate buffer 50 nM, pH 6.8 to 7.8 50 mM, $Na_2SO_4$ is added 0.5 M (equilibration buffer). Then, a ½ dilution of the sample in equilibrium buffer is added to the activated sepharose support. The elution of the retained protein (IgY polyclonal antibodies) is obtained by adding the phosphate buffer 50 mM pH 6.8 to 7.8.

Once antibodies are obtained, they are evaluated by known immunochemical techniques, such as indirect ELISA. Allergenic extracts of *Dermatophagoides pteronyssinus*, *Dermatophagoides farinae* and/or *Blomia tropicalis* mites, are diluted in PBS 1× and added to a polystyrene plate, incubated at 37° C. for 15-24 hours in a moist chamber. The plate was blocked with a blocking solution (e. g., PBS, Tween 0.05%, 5% skim milk), incubated for 1-3 hours at 37° C. in a moist chamber. Afterwards, it was washed with a washing solution (e. g., PBS, Tween 0.05%). Series of double dilutions of antibodies (IgY produced by the first method of the invention) are added to previously treated polystyrene plates and incubated for 0.5-2 hours at 37° C. in a moist chamber, followed by washes under the conditions above described. Finally, diluted 1/1000 conjugated anti-IgY antibodies are added (e. g., Anti-IgY conjugate with peroxidase), it is revealed with substrate (e. g., TMB 3,3',5,5'tetramethylbenzidine), the reaction was stopped with 1N HCl and read at a wavelength of 450 nm. The previous evaluation can also be carried out by using direct immunochemical techniques known in the art.

Additionally, in some embodiments of the invention, IgY polyclonal antibodies are labeled by labeling techniques known in the art or can form immunoconjugates such as immunoconjugates with colloidal gold particles or biotin.

3. 2. 2. Method for Detecting Mite Allergens.

The second method of the invention led to the detection of allergens in dust samples, comprising the steps of:
1. Sampling dust environments where intradomiciliary mites are present or suspected;
2. Preparation of protein extract from dust samples;
3. Development of immunochemical tests with the composition of polyclonal IgY antibodies, evaluating the presence of allergens in previously collected samples.

In step 1, a manual vacuum is used in an area of 1 to 2 m² using a separate collection bag by area to evaluate.

In stage 2, to 10-30 mg of dust, 1-3 mL of extraction buffer are added (e. g., PBS 1×-Tween 20 at 0.05% v/v), followed by stirring for 1-3 minutes at room temperature. Proteins dissolved in the aqueous phase are separated from insoluble material by centrifugation at 2700-3700 rpm for 3-8 minutes. In order to ensure complete separation, the supernatant was purified with a 0.22 micron filter, taking the supernatant for later analysis.

Figure 5:
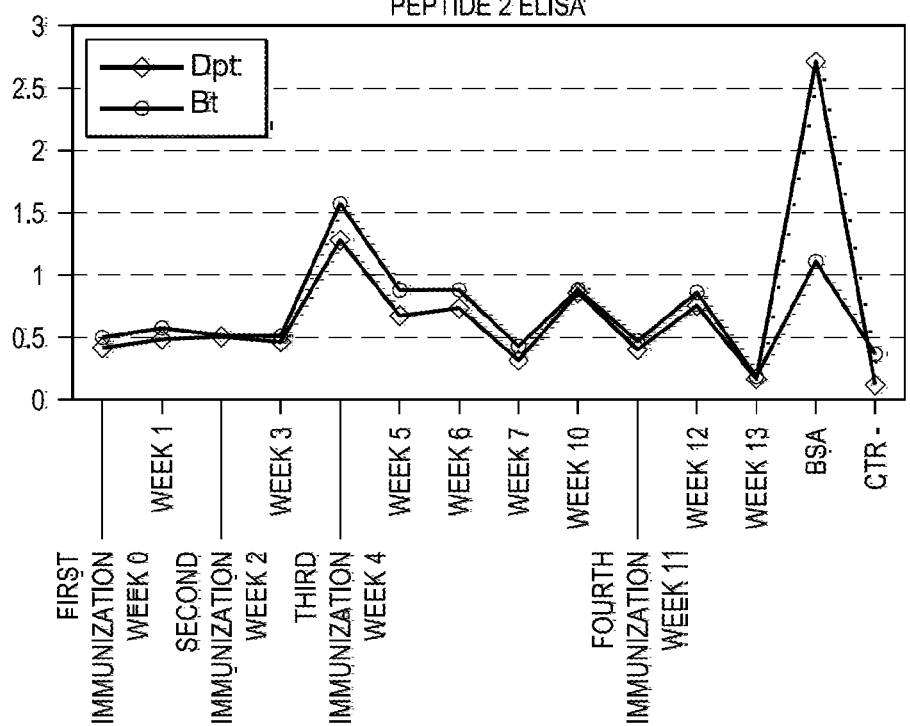

The contact of the protein extract with the IgY antibody composition and the detection of the allergen is directly made by methods known in the art, or indirectly as shown in FIG. 5.

For indirect detection, the polystyrene plate is incubated with the dust protein extract, then it is incubated again with IgY anti allergen antibodies of intradomiciliary mites of group 1 and later with conjugated anti-IgY antibody (e. g., conjugated with peroxidase), the reaction was revealed by adding the substrate (e. g., TMB) and detected at 450 nm absorbance. Detection is performed by correlating the change in color or fluorescence because of the presence of mite allergens, as shown in FIG. 15

EXAMPLE 5

Method for Obtaining a IgY Polyclonal Antibody Composition Useful as a Low Cost Diagnostic Reagent for Detecting Intradoimiciary Mite Allergens SEQ ID NO 1, SEQ ID No 2, SEQ ID No 3, SEQ ID No 4, SEQ ID NO 5, SEQ ID No 6 peptides were used or those having a 85% homology, which were emulsified to a concentration of 100 mcg/ml in complete Freund's adjuvant for the first immunization and incomplete adjuvant for subsequent immunizations.

Laying chickens of 16 to 20 weeks of age were immunized by four intramuscular immunizations in the pectoral muscles (breast) every 2 weeks for 2 months and the eggs were daily collected, labeled and stored at 4° C.

The egg yolk and white where carefully separated, measuring volumes of each; the yolk was emulsified in an equal volume of PBS and de-lipidated with 2 volumes of chloroform added, the mixture was incubated at room temperature for 2 hours, centrifuged at 3500 rpm for 15 minutes at a temperature between 17° C. and the supernatant was collected;

Antibodies were purified using a CL4B Sepharose support activated with divinylsulfone (DVS) with coupled β-mercaptoethanol (β-MESH) Two milliliters of the active support were equilibrated in phosphate buffer 50 mM pH 7.4, added with $Na_2SO_4$ 0.5 M (equilibration buffer). A 1:2 dilution of the sample in equilibrium buffer was added to the Sepharose support. The elution of the retained protein was obtained by adding phosphate buffer 50 mM pH 7.4.

The amount of protein in the extracts was quantified by the methods of Bradford and Lowry, for which a 1:5 diluted dye solution was prepared, to which 100 ml of the sample was added, the optical density (OD) is read at 595 nm. The protein concentration was determined by extrapolating the obtained OD in a titration curve (OD vs. concentration) constructed using a pattern.

EXAMPLE 6

Method for Detecting Intradomiciliary Mite Allergens

Dust samples were collected with a manual vacuum in an area of 1 to 2 m 2, keeping a ratio of 0.5 m²/min. 20 mg of each sample were diluted in 2 ml of phosphate buffer and stirred for 5 minutes; serial dilutions of supernatant were placed in a polystyrene plate, incubated at 37° C. for 18 hours in a moist chamber; blocking solution was added and incubated at 37° C. for 2 hours; double dilution series of the IgY antibodies composition obtained in the first method of the invention were added; reaction plates were incubated between 37° C. for 2 hours in a moist chamber; washes were made, anti-IgY antibodies conjugated with diluted 1/1000 radish peroxidase (HRP) were added, and the test was developed with TMB 3,3',5,5'-tetramethylenzidine substrate, the reaction was stopped with HCl 1N or by labeling the IgY antibodies that constitute the diagnostic reagent obtained by the first method of the invention with fluorophores, enzymes, precious metals, or radiolabeled ligands.

EXAMPLE 7

Production of an Immunochromatographic Test (Lateral Flow Immunoassays) with IgY-Colloidal Gold Nanoparticles Immunoconjugates Anti-oligopeptide synthetic IgY antibodies from *D. pteronyssinus, D. farinae* and *B. Tropical* mites of group 1 allergens (obtained by the first method of the invention) were labeled with 40 nm diameter colloidal gold nanoparticles. Immunoconjugates (IgY-nanoGold) were used as a detection reagent in an immunochromatographic assay, whose implementation involved the manufacturing of a test strip. The test strip consists of four sections, as described below:

ii) The area of application or "pillow sample" consists of a cellulose fiber whose function is to remove the viscous or particulate material present in the mixture and adjust the reaction conditions for immunodetection.

iii) The labeling area or "conjugate pad" is composed of fiberglass and constitutes the mobile phase of the immunoassay system, where a "dye conjugate" was lyophilized, which is the IgY anti-synthetic oligopeptide detection antibody of Der p1, Der f1 and Blot 1 allergens (obtained by the first method of the invention), conjugated to colloidal gold nanoparticles (40 nm); the IgY detection antibody specifically binds to the allergen present in the sample, forming the complex "allergen-antibody dye conjugate."

iiii) The third section (detection zone) of the strip comprises a nitrocellulose membrane and forms the solid support of the immunochromatography system. This section has two reaction zones: a primary reaction zone (T) where a mixture of Der p1 Der f1 and/or blot 1 test allergen with BSA is immobilized (allergen/BSA), and a secondary area of reaction (C) where the capture antibody (IgG anti-IgY) is immobilized. If the test allergen is present in the sample it binds to the IgY detection antibody forming the complex "allergen-dye conjugate," which moves to T-zone. Because the antibody binding sites are occupied by the allergen present in the sample, no color signal is produced in this area (positive test). The complex "allergen-dye conjugate" keeps moving to C-zone, where it binds the IgG anti IgY capture antibody, forming the complex "capture antibody-conjugate dye-antigen," which is displayed as a line in this area. In presence or absence of allergens in the sample, the signal in C-zone must be present, which constitutes a control test, that is, confirming that the test is functional or valid, regardless of a negative or positive result in T-zone.

ivi) The fourth section on the test strip comprises an "absorbent pad" that directs the side flow of the solution sample continuously upstream (see FIG. 16).

To perform this test the device disclosed in patent PCTIB2010/000176 is preferably used.

EXAMPLE 8

Production of an Immunochromatographic Test (Lateral Flow Immunoassays) with IgY-Biotine Immunoconjugates For the chromatographic immunoassay with IgY-Biotin immunoconjugates, purified antibodies dissolved in saline phosphate buffer were labeled with biotin using a NHS-LC-Biotin commercial labeling reagent (Priece, Rockford, Ill.). A straptavidin carrier protein was also prepared (BSA-streptavidin). The design of the test strip is shown in FIG. 17.

The sample preparation for the chromatographic immunoassay was performed in the same way as for indirect Elisa, in this case for interpretation of results a numeric value from 1 to 5 was given to colorimetric results of color depth, where 1 means no color and 5 the highest color intensity.

To perform this test the device disclosed in patent PCTIB2010/000176 is preferably used.

REFERENCES

1. Marasco D, Perretta G, Sabatella M, Ruvo M. Past and future perspectives of synthetic peptide libraries. Curr Protein Pept Sci. 2008 October; 9(5):447-67.
2. Kauffman H F, Tamm M, Timmerman J A, Borger P. House dust mite major allergens Der p1 and Der p5 activate human airway-derived epithelial cells by protease-dependent and protease-independent mechanisms. Clin Mol Allergy. 2006 Mar. 28; 4(1):5.
3. Egea E., Olivares M., Garavito G., Tirado F. Prevalencia de sensibilización a alergenos intra domiciliarios en pacientes con asma en la ciudad de Barranquilla. Rev Col Neumologia 2000; 12(Sup1): S184.
4. Platts-Mills T A E, Rakes G and Heymann P. the relevance of allergen exposure to the development of asthma in childhood. J Allergy Clin Immunol 2000; 105: S503-8.
5. Fernandez-Caldas E, Puerta L, et al. Mite allergens. Clin Allergy Immunol. 2004; 18:251-70.
6. International Union of Immunological societies (IUIS) Allergen Nomenclature Sub-committee. Allergen Nomenclature.
7. Chapman M D, Platts-Mills T A. Purification and characterization of the major allergen from *Dermatophagoides pteronyssinus*-antigen P1. J Immunol. 1980 August; 125 (2):587-92.
8. Heymann P W, Chapman M D, Platts-Mills T A. Antigen Der f I from the dust mite *Dermatophagoides farinae*: structural comparison with Der p I from *Dermatophagoides pteronyssinus* and epitope specificity of murine IgG and human IgE antibodies. J Immunol. 1986 Nov. 1; 137 (9):2841-7.
9. Charles J. Hackett, PhD, and Howard B. Dickler, MD. Immunologic tolerance for immune system-mediated diseases. J Allergy Clin Immunol 1999; 103:362-70.
10. Briner, T. J., Kuo, M. C., Keating, K. M., Rogers, B. L., & Greenstein, J. L. (1993). Peripheral T-cell tolerance induced in naive and primed mice by subcutaneous injection of peptides from the major cat allergen Fel d I. Proc Natl Acad Sci USA, 90, 7608-7612.
11. Hoyne, G. F., O'Hehir, R. E., Wraith, D. C., Thomas, W. R., & Lamb, J. R. (1993) Inhibition of T cell and antibody responses to house dust mite allergen by inhalation of the dominant T cell epitope in naive and sensitized mice. J Exp Med, 178, 1783-1788.
12. Astori, M., von Garnier, C., Kettner, A., Dufour, N., Corradin, G., & Spertini, F. (2000). Inducing tolerance by intranasal administration of long peptides in naive and primed CBA/J mice. J Immunol, 165, 3497-3505.
13. Oldfield W L, Kay A B, Larche M. Allergen-derived T cell peptide induced late asthmatic reactions precede the induction of antigen-specific hyporesponsiveness in atopic allergic asthmatic subjects. J Immunol 2001; 167:1734-9.
14. Norman P S, Ohman J L, Long A A, Creticos P S, Gefter M A, Shaked Z, et al. Treatment of cat allergy with T-cell reactive peptides. Am J Respir Crit Care Med 1996; 154: 1623-8.
15. Simons F E, Imada M, Li Y, Watson W T, HayGlass K T. Fel d 1 peptides: effect on skin tests and cytokine synthesis in cat-allergic human subjects. Int Immunol 1996; 8:1937-45.
16. Leslie G A, Clem L W. Philogeny of immunoglobulin structure and function. III. Immunoglobulins of the chicken. J Exp Med. 1969; 130: 1337-52.
17. Warr G W, Margor K E, et al. IgY: clues to the origins of modern antibodies. Immunol Today 1995; 16:392-8.
18. Jensenius J C, Andersen I, Hau J, Crone M, et al. Eggs: conveniently packaged antibodies. Methods for purification of yolk IgG. J Immunol Meths 1981; 46:63-8.
19. Polson A, Von Wechmar M B, et al. Isolation of viral IgY antibodies from yolks of immunized hens. Immunol Comm 1980; 9:475-93.

20. Burley M W, Cook W H. Isolation and composition of avian yolk granules and their constituents alpha and beta-lipovitellins. Can J Biochem Physiol 1961; 39:1295302.
21. Margor K E, et al. One gne encodes the heavy chains for three different forms of IgY in the duck. J Immunol 1994; 153: 5549-55.
22. Finlay W. J. J., de Vore N. C., Dobrovolskaia E. N., Gam A., Goodyear C. S. and Slate J. E. Exploiting the avian immunoglobulin system to simplify the generation of recombinant antibodies to allergenic proteins. Clinical & Experimental Allergy 2005; 35: 1040.
23. Blais B. W., L. M. Phillippe. A Cloth-based Enzyme Immunoassay for Detection of Peanut Proteins in Foods. Food and Agriculture immunology 2000; 12(3): 243-248.
24. Burton W, Mahomed O, et al. Deteccion of Brazil nut proteins in foods by enzyme immunoassay. Food and agricultural Immunology 2002; 14(2): 163-168.
25. Hermanson G T, Mallia A, Smith P. Immobilized affinity ligand techniques. San Diego: Academic Press; 1992. P. 110-6.
26. Towbin H, Staehelin T, Gordon J. Electrophoretic transfer of proteins from polyacrylamide gels to nitrocellulose sheets: procedure and some applications. Proc Natl Acad Sci USA 1979; 76:4350-4.
27. Cheong N, et al. Lack of human IgE cross-reactivity between mite allergens Blo t 1 and Der p 1. Allergy 2003; 58:912-920.
28. Chua K Y, et al. Sequence analysis of cDNA coding for a major house dust mite allergen, Der p I. Homology with cystine protease. J Exp Med 1988; 167:175-182.
29. Schulz, O., H. F. Sewell, F. Shakib. 1999. The interaction between the dust mite antigen Der p 1 and cell-signalling molecules in amplifying allergic disease. *Clin. Exp. Allergy* 29:439.-444.
30. Heymann P W, Chapman M D, Platts-Mills T A E. Antigen Der f I from the house dust mite *Dermatophagoides farinae*. In structural comparison with Der p I from *Dermatophagoides pteronyssinus* and human IgE epitope specificity of murine IgG and human IgE antibodies. J Immunol 1986; 137:2841-2847.
31. Alberse R C. Structural biology of allergens. J Allergy Clin Immunol 2000; 106:228-238.
32. Chapman M D, et al. Nomenclature and structural biology of allergens J Allergy Clin Immunol 2007; 119: 414-20.
33. Marsh D G., Goodfriend L., King T P., et al. Allergen nomenclature. Bull WHO 1986; 64:767.
34. Pómes A. Intrinsic properties of allergens and environmental exposure as determinants of allergenicity. Allergy 2002; 57: 673-679.
35. Woodfolk J A., Wheatley L M., Piyasena R V., et al. *Trichophyton* antigens associated with IgE antibodies and delayed type hypersensitivity: sequence homology to two families of serine proteinases. J Biol Chem 1998; 273: 29489.
36. Schellenberg R R., Adkinson N F. Measurement of absolute amounts of antigen-specific human IgE by a radioallergosorbent test (RAST) elution technique. J Immunol 1975; 115: 1577.
37. Bohle B., Schwihla H., Hu H Z., et al. long lived $T_{h2}$ clones specific for seasonal and perennial allergens can be detected in blood an skin by their TCR-hypervariable regions. J Immunol 1998; 160: 2020.
38. Ring J, Kramer U, Schafer T et al. Why are allergies increasing? Curr Opin Immunol 2001; 13: 701-708.
39. Sánchez-De la Vega W, Sánchez-Medina M, Lucena G, Vanella L, Moreno G, Albornoz A, et al. Manual Latinoamericano de Alergia e Inmunologia 1987: primera edición. Colciencias ISBN 958-608-045-5. Pags: 39-60.
40. Weghofer M, Thomas W R, Pittner G, Horak F, Valenta R, Vrtala S. Comparison of purified *Dermatophagoides pteronyssinus* allergens and extract by two-dimensional immunoblotting and quantitative immunoglobulin E inhibitions. Clin Exp Allergy. 2005 October; 35(10):1384-91.
41. Arlian L G, Bernstein D, Bernstein I L, Friedman S, Grant A, Lieberman P, Lopez M, Metzger J, Platts-Mills T, Schatz M, et al. Prevalence of dust mites in the homes of people with asthma living in eight different geographic areas of the United States. J Allergy Clin Immunol. 1992 September; 90(3 Pt 1):292-300.
42. Fernandez-Caldas E, Lockey R F. *Blomia tropicalis*, a mite whose time has come. Allergy. 2004 November; 59(11):1161-4.
43. International Union of Immunological societies (IUIS) Allergen Nomenclature Sub-committee. Allergen Nomenclature. www.allergen.org
44. Heymann P W, Chapman M D, Platts-Mills T A E. Antigen Der f I from the house dust mite *Dermatophagoides farinae*. In structural comparison with Der p I from *Dermatophagoides pteronyssinus* and human IgE epitope specificity of murine IgG and human IgE antibodies. J Immunol 1986; 137:2841-2847.
45. Jensenius J C, Andersen I, Hau J, Crone M, et al. Eggs: conveniently packaged antibodies. Methods for purification of yolk IgG. J Immunol Meths 1981; 46:63-8.
46. Thoma W R, et al. Cloning and expression of DNA coding for the major house dust mite allergen Der p 1 in *E. coli*. Int Arch Allergy Appl Immunol 1986; 85:127-129.
47. Chua K Y, et al. Sequence analysis of cDNA coding for a major house dust mite allergen, Der p I. Homology with cystine protease. J Exp Med 1988; 167:175-182.
48. Dilworth R J, et al. Sequence analysis of cDNA coding for a major house dust mite allergen. Der f I. Clin Exp Allergy 1991; 21:25-32.
49. Schulz, O., H. F. Sewell, F. Shakib. 1999. The interaction between the dust mite antigen Der p 1 and cell-signalling molecules in amplifying allergic disease. *Clin. Exp. Allergy* 29:439.-444.
50. Lind P, Lowenstein H. Identification of allergens in *Dermatophagoides pteronssinus* mite body extract by crossed radioimmunoelectrophoresis with two different rabbit antibody pools. Scand J Immunol 1983; 17:263-273.
51. Lind W R, et al. Purification and partial characterization of two major allergens from the house dust mite *Dermatophagoides pteronyssinus*. J Allergy Clin Immunol 1988; 76:753-761.
52. Vand der ee J S, et al. Skin tests and histamine release with P 1-depleted *Dermatophagoides pteronyssinus* body extracts and purified P1. J Allergy Clin Immunol 1988; 81:884-895.
53. Barrett A J, Rawlings N D. Evolutionary lines of cysteine peptidases. Biol Chem. 2001 May; 382(5):727-33.
54. Chua, K. Y., G. A. Stewart, W. R. Thomas, R. J. Simpson, R. J. Dilworth, T. M. Plozza, K. J. Turner. 1988. Sequence analysis of cDNA coding for a major house dust mite allergen, Der p 1: homology with cysteine proteases. *J. Exp. Med.* 167:175.-182.
55. Smith W A, et al. Allergens of wild house dust mites: environmental Der p 1 and Der p 2 sequence polymorphisms. J Allergy Clin Immunol 2001; 107:285-992.
56. Jarnicki A G, et al. Stimulatory and inhibitory epitopes in the T cell responses of mice to Der p 1. Clin Exp Allergy 2002; 32:942-950.

57. Vernet, T., H. E. Khouri, P. Laflamme, D. C. Tessier, R. Musil, B. J. Gour-Salin, A. C. Storer, D. Y. Thomas. 1991. Processing of the papain precursor: purification of the zymogen and characterization of its mechanism of processing. *J. Biol. Chem.* 266:21451.-21457.

58. Ikemura, H., H. Takagi, M. Inouye. 1987. Requirement of pro-sequence for the production of active subtilisin E in *Escherichia coli. J. Biol. Chem.* 262:7859.-7864.

59. Menard, R., J. Carriere, P. Laflamme, C. Plouffe, H. E. Khouri, T. Vernet, D. C. Tessier, D. Y. Thomas, A. C. Storer. 1991. Contribution of the glutamine 19 side chain to transition-state stabilization in the oxyanion hole of papain. *Biochemistry* 30:8924.-8928.

60. Meno K, Thorsted P B, Ipsen H, Kristensen O, Larsen J N, Spangfort M D, Gajhede M, Lund K. The Crystal Structure of Recombinant proDer p 1, a Major House Dust Mite Proteolytic. *J Immunol.* 2005; 175: 3835-3845.

61. De Halleux, S., Stura, E., VanderElst, L., Carlier, V., Jacquemin, M., Saint-Remy, J. -M. Three-dimensional structure and IgE-binding properties of mature fully active Der p 1, a clinically relevant major allergen *J. Allergy Clin. Immunol.* 2006; 117: 571-576.

62. Storer, A. C., R. Menard. 1994. Catalytic mechanism in papain family of cysteine peptidases. *Methods Enzymol.* 244:486.-500.

63. Barrett, A. J., N. D. Rawlings, J. F. Woesser. 1998. Cysteine peptidases. *Handbook of Proteolytic Enzymes* 543.-798. Academic Press, London.

64. Smith W A, Hales B J, Jarnicki A G, Thomas W R. Allergens of wild house dust mites: environmental Der p 1 and Der p 2 sequence polymorphisms. J Allergy Clin Immunol 2001; 107:985-92.

65. Schultz et al. SMART, a simple modular architecture research tool: Identification of signaling domains. (1998) *Proc. Natl. Acad. Sci. USA* 95, 5857-5864.

66. Letunic et al. SMART 5: domains in the context of genomes and networks (2006) *Nucleic Acids Res* 34, D257-D260.

67. Chapman M D, Platts-Mills T A. Purification and characterization of the major allergen from *Dermatophagoides pteronyssinus*-antigen P1. J Immunol. 1980 August; 125 (2):587-92.

68. Heymann P W, Chapman M D, Platts-Mills T A. Antigen Der f I from the dust mite *Dermatophagoides farinae*: structural comparison with Der p I from *Dermatophagoides pteronyssinus* and epitope specificity of murine IgG and human IgE antibodies. J Immunol. 1986 Nov. 1; 137 (9):2841-7.

69. Furmonaviciene R, Shakib F. The molecular basis of allergenicity: comparative analysis of the three dimensional structures of diverse allergens reveals a common structural motif. Mol Pathol. 2001 June; 54(3):155-9.

70. Furmonaviciene R, Sewell H F, Shakib F. Comparative molecular modelling identifies a common putative IgE epitope on cysteine protease allergens of diverse sources. Clin Exp Allergy. 2000 September; 30(9):1307-13.

71. Schellenberg R R., Adkinson N F. Measurement of absolute amounts of antigen-specific human IgE by a radioallergosorbent test (RAST) elution technique. J Immunol 1975; 115: 1577.

72. Bohle B., Schwihla H., Hu H Z., et al. long lived $T_{h2}$ clones specific for seasonal and perennial allergens can be detected in blood an skin by their TCR-hypervariable regions. J Immunol 1998; 160: 2020.

73. Goodman R E. Practical and predictive bioinformatics methods for the identification of potentially cross-reactive protein matches. Mol Nutr Food Res. 2006 July; 50(7): 655-60.

74. Thomas W R, Smith W A, Hales B J. The allergenic specificities of the house dust mite. Chang Gung Med J. 2004 August; 27(8):563-9.

75. Simpson A, Green R, Custovic A, Woodcock A, Arruda L K, Chapman M D. Skin test reactivity to natural and recombinant *Blomia* and *Dermatophagoides* spp. allergens among mite allergic patients in the UK. Allergy. 2003 January; 58(1):53-6.

76. Pauli G, Bessot J C. The fight against mites. Allergy Today 1998; 2(7):7-9.

77. Fernández E, Puerta L, Mercado D, Lockey R F, Caraballo L. Mite fauna Der p1, Der f1 and *Blomia tropicalis* allergen in a tropical environment. Clin Exp Allergy 1993; 23(4): 2992-7.

78. Carswell F. House dust allergy. ACI Int 1996; 8(5-6):169-71.

79. Marchler-Bauer A, Bryant S H. "*CD-Search: protein domain annotations on the fly.*", Nucleic Acids Res. 2004; 32: 27-331.

80. Thomas W R, Hales B J, Smith W A. Recombinant allergens for analysing T-cell responses. Methods. 2004 March; 32(3):255-64.

81. Aalberse R C. Structural features of allergenic molecules. Chem Immunol Allergy. 2006; 91:134-46.

82. Collazo M E, Diaz A M. Monoclonal antibodies against whole body extract of the dust mite *Blomia tropicalis*. P R Health Sci J. 2003 December; 22(4):345-51.

83. Rokni M B, Massoud J, Hanilo A. Comparison of adult somatic and cysteine proteinase antigens of *Fasciola gigantica* in enzyme linked immunosorbent assay for serodiagnosis of human fasciolosis. Acta Trop. 2003 September; 88(1):69-75.

84. Hong Wan, Helen L. Winton, Christian Soeller, Euan R. Tovey, Dieter C. Gruenert, Philip J. Thompson, Geoffrey A. Stewart, Graham W. Taylor, David R. Garrod, Mark B. Cannell, and Clive Robinson Der p 1 facilitates transepithelial allergen delivery by disruption of tight junctions J. Clin. Invest., July 1999; 104: 123-133.

85. Wan, Winton, Soeller, Gruenert, Thompson, Cannell, Stewart, Garrod, Robinson (2000) Quantitative structural and biochemical analyses of tight junction dynamics following exposure of epithelial cells to house dust mite allergen Der p 1 Clinical & Experimental Allergy 30 (5), 685-698.

86. Tomee J F C, van Weissenbruch R, de Monchy J G R, Kauffman H F. Interactions between inhalant allergen extracts and airway epithelial cells: effect on cytokine production and cell detachment. J Allergy Clin Immunol 102: 75-85 (1998).

87. Shakib F, Schulz O, Sewell H F. A mite subversive: cleavage of CD23 and CD25 by Der p 1 enhances allergenicity. Immunol Today 1998; 19:313.

88. Abbas, A. K., K. M. Murphy, and A. Sher. 1996. Functional diversity of helper T lymphocytes. Nature. 383:787-793. [Abstract]

89. Schulz O, Sewell H F, Shakib F. Proteolytic cleavage of CD25, the a subunit of the human T cell Interleukin 2 receptor, by Der p 1, a major mite allergen with cysteine protease activity. J Exp Med 1998; 187:271±5. [Abstract]

90. Machado D C, Horton D, Harrop R et al. Potential allergens stimulate the release of mediators of the allergic response from cells of mast cell lineage in the absence of sensitization with antigen-specific IgE. Eur J Immunol 1996; 26:2972±80.
91. G. Roberts, C. Peckitt†, K. N. Relationship between aeroallergen and food allergen sensitization in childhood. Clinical & Experimental Allergy 2005: (35), 7, Pages 933-940.
92. Stelmach I, Jerzynska J, Stelmach W et al. Cockroach allergy and exposure to cockroach allergen in Polish children with asthma. Allergy 2002; 57: 701-5.
93. Santos A B, Chapman M D, Aalberse R C et al. Cockroach allergens and asthma in Brazil: identification of tropomyosin as a major allergen with potential cross-reactivity with mite and shrimp allergens. J Allergy Clin Immunol 1999; 104: t-37
94. Guidos F, V. Almeida A. Polinosis y aeroalérgenos. Alergia asma e inmunologia pediátrica. 2005; 14 (2): pp 52-55.
95. N. deVore, W. Finlay, E. Cloning and Analysis of Mono-Specific scFv Fragments From Chicken to Allergenic Proteins of Periplaneta Americana (American Cockroach). J Allergy and Clinical immunology 2005; 113 (2):5297.
96. Finlay, W. J. J.; deVore, N. C. Exploiting the avian immunoglobulin system to simplify the generation of recombinant antibodies to allergenic proteins. Clinical & Experimental Allergy. 2005, 35(8):1040-1048.
97. J. Bousquet, B. Björkstén, C. A. F. M. Bruijnzeel-Koomen, A. Huggett, C. Ortolani, J. O. Warner, M. Smith. Scientific criteria and the selection of allergenic foods for product labeling. Allergy 53 (1998) 3-21.
98. M. Besler, Determination of allergens in foods Trends Anal. Chem. 20 (2001) 662.
99. Helm R M, Burks A W. Food allergens. Clin Allergy Immunol. 2008; 21:219-35.
100. Zarkadas, M., Scott, F. W., Salminen, J., & Ham Pong, A. (1999). Common allergenic foods and their labelling in Canada—a review. Canadian Journal of Allergy and Clinical Immunology, 4, 118-141.
101. Burton W. Blais, Melissa Gaudreault, Lucille M. Phillippe. Multiplex enzyme immunoassay system for the simultaneous detection of multiple allergens in foods. Food Control 14 (2003) 43-47.
102. HOURIHANE, J. O'B., KILBURN, S. A., NORDLEE, J. A., HEFLE, S. L., TAYLOR, S. L. & WARNER, J. O. (1997) An evaluation of the sensitivity of subjects with peanut allergy to very low doses of peanut protein: a randomized, double-blind, placebo-controlled food challenge study, Journal of Allergy and Clinical Immunology, 100, 596-600.
103. B. W. BLAIS AND L. M. PHILLIPPE. A Cloth-based Enzyme Immunoassay for Detection of Peanut Proteins in Foods. *Food and Agricultural Immunology* (2000) 12, 243-248.
104. E. Drs a, S. Baumgartner a, M. Bremer. Detection of hidden hazelnut protein food by IgY-based indirect competitive enzyme-immunoassay. Analytica Chimica Acta 520 (2004) 223-228.
105. Burton W. Blais, Melissa Gaudreault, Lucille M. Phillippe. Multiplex enzyme immunoassay system for the simultaneous detection of multiple allergens in foods. Food Control 14 (2003) 43-47

The invention claimed is:

1. A method for producing an IgY antibody composition comprising the steps of:
   a) preparing an immunogenic composition consisting essentially of at least one peptide selected from the group consisting of SEQ ID Nos. 2, 3, 4, 5 and 6;
   b) hyperimmunizing a bird with more than one immunization with said immunogenic composition;
   c) extracting IgY polyclonal antibodies from egg yolk of an egg laid by the bird; and
   d) purifying IgY polyclonal antibodies.

2. The method of claim 1, where in step a), the preparation of the immunogenic composition is carried out by emulsification of the peptide with Freund's complete adjuvant for a first immunization in the hyperimmunization step b).

3. The method of claim 1, where in step a), the preparation of the immunogenic composition is carried out by emulsification of the peptide with Freund's incomplete adjuvant for subsequence immunizations in the hyperimmunization step b).

4. The method of claim 1, where in step b), the hyperimmunization is carried out in Hy Line Brown commercial line chickens.

5. The method of claim 1, where in the step b), the hyperimmunization is performed in hen pectoral muscles at 15-day intervals.

6. The method of claim 1, where the extraction in step c) is carried out using chloroform and phosphate saline buffer for the separation of antibodies from egg yolk.

7. The method of claim 1, where the purification in step d) is performed using a CL4B Sepharaose column activated with divinylsulfone coupled with β-Mercaptoethanol, where active support is equilibrated in phosphate buffer then adding $Na_2SO_4$, and then adding a dilution of the sample in equilibrium buffer, and the elution of polyclonal IgY antibodies is obtained by adding phosphate buffer.

8. The method of claim 1, further comprising the step of labeling the polyclonal IgY antibodies.

9. The method of claim 1, further comprising the step of generating immunoconjugates of polyclonal IgY antibodies.

10. The method of claim 8, where the labeling is carried out using fluorochromes, enzymes, precious metals or radiolabeled ligands.

11. The method of claim 9, where the immunoconjugates are selected from the group consisting of IgY-gold nanoparticle immunoconjugates and IgY-biotin immunoconjugates.

12. The method of claim 1, further comprising the step of validating the antibodies with crude allergen extracts and purified allergens through immunochemical assays.

13. A composition of polyclonal IgY antibodies obtained by the method of claim 1, where polyclonal IgY antibodies are dust mite specific.

14. An analytical kit for detecting dust mites comprising the antibody composition of claim 13.

15. The method of claim 1, wherein the peptide in step a) has SEQ ID NO. 2.

16. The method of claim 1, wherein the peptide in step a) has SEQ ID NO. 3.

17. The method of claim 1, wherein the peptide in step a) has SEQ ID NO. 4.

18. The method of claim 1, wherein the peptide in step a) has SEQ ID NO. 5.

19. The method of claim 1, wherein the peptide in step a) has SEQ ID NO. 6.

\* \* \* \* \*

SEQUENCE LISTING

```
<160> NUMBER OF SEQ ID NOS: 10

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide

<400> SEQUENCE: 1

Thr Asn Ala Cys Ser Ile Asn Gly Asn Ala Pro Ala Glu Ile Asp Leu
1               5                   10                  15

Arg Gln Met Arg
            20

<210> SEQ ID NO 2
<211> LENGTH: 17
<212> TYPE: PRT
<213> ORGANISM: Artificial Sequence
<220> FEATURE:
<223> OTHER INFORMATION: Synthetic peptide

<400> SEQUENCE: 2

Pro Ile Arg Met Gln Gly Gly Cys Gly Ser Cys Trp Ala Phe Ser Gly
1               5                   10                  15

Val

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide
```

-continued

<400> SEQUENCE: 3

Asp Tyr Trp Ile Val Arg Asn Ser Trp Asp Thr Asn Trp Gly Asp Asn
1               5                   10                  15

Gly Tyr Gly Tyr
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide

<400> SEQUENCE: 4

Phe Arg His Tyr Asp Gly Arg Thr Ile Ile Gln Arg Asp Asn Gly Tyr
1               5                   10                  15

Gln Pro Asn Tyr
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

<400> SEQUENCE: 5

Ile Pro Ala Asn Phe Asp Trp Arg Gln Lys Thr His Val Asn Pro Ile
1               5                   10                  15

Arg Asn Gln Gly
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6

Ala His Phe Arg Asn Leu Arg Lys Gly Ile Leu Arg Gly Ala Gly Tyr
1               5                   10                  15

Asn Asp Ala Gln
            20

<210> SEQ ID NO 7
<211> LENGTH: 320
<212> TYPE: PRT
<213> ORGANISM: Dermatophagoides pteronyssinus

<400> SEQUENCE: 7

Met Lys Ile Val Leu Ala Ile Ala Ser Leu Leu Ala Leu Ser Ala Val
1               5                   10                  15

Tyr Ala Arg Pro Ser Ser Ile Lys Thr Phe Glu Glu Tyr Lys Lys Ala
            20                  25                  30

Phe Asn Lys Ser Tyr Ala Thr Phe Glu Asp Glu Glu Ala Ala Arg Lys
        35                  40                  45

Asn Phe Leu Glu Ser Val Lys Tyr Val Gln Ser Asn Gly Gly Ala Ile
    50                  55                  60

Asn His Leu Ser Asp Leu Ser Leu Asp Glu Phe Lys Asn Arg Phe Leu
65                  70                  75                  80

```
Met Ser Ala Glu Ala Phe Glu His Leu Lys Thr Gln Phe Asp Leu Asn
                85                  90                  95

Ala Glu Thr Asn Ala Cys Ser Ile Asn Gly Asn Ala Pro Ala Glu Ile
            100                 105                 110

Asp Leu Arg Gln Met Arg Thr Val Thr Pro Ile Arg Met Gln Gly Gly
            115                 120                 125

Cys Gly Ser Cys Trp Ala Phe Ser Gly Val Ala Ala Thr Glu Ser Ala
            130                 135                 140

Tyr Leu Ala Tyr Arg Asn Gln Ser Leu Asp Leu Ala Glu Gln Glu Leu
145                 150                 155                 160

Val Asp Cys Ala Ser Gln His Gly Cys His Gly Asp Thr Ile Pro Arg
                165                 170                 175

Gly Ile Glu Tyr Ile Gln His Asn Gly Val Val Gln Glu Ser Tyr Tyr
            180                 185                 190

Arg Tyr Val Ala Arg Glu Gln Ser Cys Arg Arg Pro Asn Ala Gln Arg
            195                 200                 205

Phe Gly Ile Ser Asn Tyr Cys Gln Ile Tyr Pro Pro Asn Val Asn Lys
            210                 215                 220

Ile Arg Glu Ala Leu Ala Gln Thr His Ser Ala Ile Ala Val Ile Ile
225                 230                 235                 240

Gly Ile Lys Asp Leu Asp Ala Phe Arg His Tyr Asp Gly Arg Thr Ile
                245                 250                 255

Ile Gln Arg Asp Asn Gly Tyr Gln Pro Asn Tyr His Ala Val Asn Ile
            260                 265                 270

Val Gly Tyr Ser Asn Ala Gln Gly Val Asp Tyr Trp Ile Val Arg Asn
            275                 280                 285

Ser Trp Asp Thr Asn Trp Gly Asp Asn Gly Tyr Gly Tyr Phe Ala Ala
            290                 295                 300

Asn Ile Asp Leu Met Met Ile Glu Glu Tyr Pro Tyr Val Val Ile Leu
305                 310                 315                 320

<210> SEQ ID NO 8
<211> LENGTH: 321
<212> TYPE: PRT
<213> ORGANISM: Dermatophagoides farinae

<400> SEQUENCE: 8

Met Lys Phe Val Leu Ala Ile Ala Ser Leu Leu Val Leu Ser Thr Val
1               5                   10                  15

Tyr Ala Arg Pro Ala Ser Ile Lys Thr Phe Glu Glu Phe Lys Lys Ala
            20                  25                  30

Phe Asn Lys Asn Tyr Ala Thr Val Glu Glu Glu Glu Val Ala Arg Lys
            35                  40                  45

Asn Phe Leu Glu Ser Leu Lys Tyr Val Glu Ala Asn Lys Gly Ala Ile
            50                  55                  60

Asn His Leu Ser Asp Leu Ser Leu Asp Glu Phe Lys Asn Arg Tyr Leu
65                  70                  75                  80

Met Ser Ala Glu Ala Phe Glu Gln Leu Lys Thr Gln Phe Asp Leu Asn
                85                  90                  95

Ala Glu Thr Ser Ala Cys Arg Ile Asn Ser Val Asn Val Pro Ser Glu
            100                 105                 110

Leu Asp Leu Arg Ser Leu Arg Thr Val Thr Pro Ile Arg Met Gln Gly
            115                 120                 125

Gly Cys Gly Ser Cys Trp Ala Phe Ser Gly Val Ala Ala Thr Glu Ser
            130                 135                 140
```

```
Ala Tyr Leu Ala Tyr Arg Asn Thr Ser Leu Asp Leu Ser Glu Gln Glu
145                 150                 155                 160

Leu Val Asp Cys Ala Ser Gln His Gly Cys His Gly Asp Thr Ile Pro
                165                 170                 175

Arg Gly Ile Glu Tyr Ile Gln Gln Asn Gly Val Val Glu Glu Arg Ser
            180                 185                 190

Tyr Pro Tyr Val Ala Arg Glu Gln Gln Cys Arg Arg Pro Asn Ser Gln
        195                 200                 205

His Tyr Gly Ile Ser Asn Tyr Cys Gln Ile Tyr Pro Pro Asp Val Lys
    210                 215                 220

Gln Ile Arg Glu Ala Leu Thr Gln Thr His Thr Ala Ile Ala Val Ile
225                 230                 235                 240

Ile Gly Ile Lys Asp Leu Arg Ala Phe Gln His Tyr Asp Gly Arg Thr
                245                 250                 255

Ile Ile Gln His Asp Asn Gly Tyr Gln Pro Asn Tyr His Ala Val Asn
            260                 265                 270

Ile Val Gly Tyr Gly Ser Thr Gln Gly Val Asp Tyr Trp Ile Val Arg
        275                 280                 285

Asn Ser Trp Asp Thr Thr Trp Gly Asp Ser Gly Tyr Gly Tyr Phe Gln
    290                 295                 300

Ala Gly Asn Asn Leu Met Met Ile Glu Gln Tyr Pro Tyr Val Val Ile
305                 310                 315                 320

Met

<210> SEQ ID NO 9
<211> LENGTH: 221
<212> TYPE: PRT
<213> ORGANISM: Blomia tropicalis

<400> SEQUENCE: 9

Ile Pro Ala Asn Phe Asp Trp Arg Gln Lys Thr His Val Asn Pro Ile
1               5                   10                  15

Arg Asn Gln Gly Gly Cys Gly Ser Cys Trp Ala Phe Ala Ala Ser Ser
                20                  25                  30

Val Ala Glu Thr Leu Tyr Ala Ile His Arg His Gln Asn Ile Ile Leu
            35                  40                  45

Ser Glu Gln Glu Leu Leu Asp Cys Thr Tyr His Leu Tyr Asp Pro Thr
        50                  55                  60

Tyr Lys Cys His Gly Cys Gln Ser Gly Met Ser Pro Glu Ala Phe Lys
65                  70                  75                  80

Tyr Met Lys Gln Lys Gly Leu Leu Glu Glu Ser His Tyr Pro Tyr Lys
                85                  90                  95

Met Lys Leu Asn Gln Cys Gln Ala Asn Ala Arg Gly Thr Arg Tyr His
            100                 105                 110

Val Ser Ser Tyr Asn Ser Leu Arg Tyr Arg Ala Gly Asp Gln Glu Ile
        115                 120                 125

Gln Ala Ala Ile Met Asn His Gly Pro Val Val Ile Tyr Ile His Gly
130                 135                 140

Thr Glu Ala His Phe Arg Asn Leu Arg Lys Gly Ile Leu Arg Gly Ala
145                 150                 155                 160

Gly Tyr Asn Asp Ala Gln Ile Asp His Ala Val Val Leu Val Gly Trp
                165                 170                 175

Gly Thr Gln Asn Gly Ile Asp Tyr Trp Ile Val Arg Thr Ser Trp Gly
            180                 185                 190
```

```
Thr Gln Trp Gly Asp Ala Gly Tyr Gly Phe Val Glu Arg His His Asn
        195                 200                 205

Ser Leu Gly Ile Asn Asn Tyr Pro Ile Tyr Ala Ser Leu
        210                 215                 220

<210> SEQ ID NO 10
<211> LENGTH: 222
<212> TYPE: PRT
<213> ORGANISM: Dermatophagoides pteronyssinus

<400> SEQUENCE: 10

Thr Asn Ala Cys Ser Ile Asn Gly Asn Ala Pro Ala Glu Ile Asp Leu
1               5                   10                  15

Arg Gln Met Arg Thr Val Thr Pro Ile Arg Met Gln Gly Gly Cys Gly
            20                  25                  30

Ser Cys Trp Ala Phe Ser Gly Val Ala Ala Thr Glu Ser Ala Tyr Leu
        35                  40                  45

Ala Tyr Arg Gln Gln Ser Leu Asp Leu Ala Glu Gln Glu Leu Val Asp
    50                  55                  60

Cys Ala Ser Gln His Gly Cys His Gly Asp Thr Ile Pro Arg Gly Ile
65                  70                  75                  80

Glu Tyr Ile Gln His Asn Gly Val Val Gln Glu Ser Tyr Tyr Arg Tyr
                85                  90                  95

Val Ala Arg Glu Gln Ser Cys Arg Arg Pro Asn Ala Gln Arg Phe Gly
            100                 105                 110

Ile Ser Asn Tyr Cys Gln Ile Tyr Pro Pro Asn Ala Asn Lys Ile Arg
        115                 120                 125

Glu Ala Leu Ala Gln Thr His Ser Ala Ile Ala Val Ile Ile Gly Ile
    130                 135                 140

Lys Asp Leu Asp Ala Phe Arg His Tyr Asp Gly Arg Thr Ile Ile Gln
145                 150                 155                 160

Arg Asp Asn Gly Tyr Gln Pro Asn Tyr His Ala Val Asn Ile Val Gly
            165                 170                 175

Tyr Ser Asn Ala Gln Gly Val Asp Tyr Trp Ile Val Arg Asn Ser Trp
        180                 185                 190

Asp Thr Asn Trp Gly Asp Asn Gly Tyr Gly Tyr Phe Ala Ala Asn Ile
    195                 200                 205

Asp Leu Met Met Ile Glu Glu Tyr Pro Tyr Val Val Ile Leu
    210                 215                 220
```